(12) United States Patent
Svanborg et al.

(10) Patent No.: US 10,287,585 B2
(45) Date of Patent: May 14, 2019

(54) THERAPY

(71) Applicant: LINNANE PHARMA AB, Malmo (SE)

(72) Inventors: Catharina Svanborg, Malmo (SE); Manoj Puthia, Lund (SE)

(73) Assignee: Linnane Pharma AB, Malmo (SE)

( * ) Notice: Subject to any disclaimer, the term of this patent is extended or adjusted under 35 U.S.C. 154(b) by 7 days.

(21) Appl. No.: 15/561,658

(22) PCT Filed: Mar. 24, 2016

(86) PCT No.: PCT/IB2016/051674
§ 371 (c)(1),
(2) Date: Sep. 26, 2017

(87) PCT Pub. No.: WO2016/157044
PCT Pub. Date: Oct. 6, 2016

(65) Prior Publication Data
US 2018/0112215 A1    Apr. 26, 2018

(30) Foreign Application Priority Data

Mar. 29, 2015 (GB) .................................. 1505382.0

(51) Int. Cl.
| | | |
|---|---|---|
| A61K 48/00 | (2006.01) | |
| C07H 21/04 | (2006.01) | |
| C07H 21/02 | (2006.01) | |
| C12N 15/113 | (2010.01) | |
| A61P 13/12 | (2006.01) | |
| A61P 31/04 | (2006.01) | |

(52) U.S. Cl.
CPC ............ *C12N 15/113* (2013.01); *A61P 13/12* (2018.01); *A61P 31/04* (2018.01); *C12N 2310/14* (2013.01); *C12N 2320/34* (2013.01)

(58) Field of Classification Search
CPC .... C12N 15/113; C12N 15/111; A61K 31/713
See application file for complete search history.

(56) References Cited

FOREIGN PATENT DOCUMENTS

| WO | 01/18039 A2 | 3/2001 |
| WO | 2014/184735 A1 | 11/2014 |
| WO | 2015/018698 A1 | 2/2015 |
| WO | 2016/157044 A1 | 10/2016 |

OTHER PUBLICATIONS

Agace et al., "Interleukin-8 and the Neutrophil Response to Mucosal Gram-negative Infection", Journal of Clinical Investigation, 1993, pp. 780-785, vol. 92.
Bolstad et al., "A comparison of normalization methods for high density oligonucleotide array data based on variance and bias", Bioinformatics, 2003, pp. 185-193, vol. 19. No. 2.
Buss et al., "Essential Role of Mitochondrial Antiviral Signaling, IFN Regulatory Factor (IRF)3, and IRF7 in Chlamydophila pneumoniae-Mediated IFN-β Response and Control of Bacterial Replication in Human Endothelial Cells", The Journal of Immunology, 2010, pp. 3072-3078, vol. 184, No. 6.
Chua et al., "A novel normalization method for effective removal of systematic variation in microarray data", Nucleic Acids Research, 2006, e38, pp. 1-7, vol. 34, No. 5.
Fischer et al., "Pathogen Specific, IRF3-Dependent Signaling and Innate Resistance to Human Kidney Infection", PLoS Pathogens, 2010, e1001109, pp. 1-17, vol. 6, No. 9.
Hagberg et al., "Ascending, Unobstructed Urinary Tract Infection in Mice Caused by Pyelonephritogenic *Escherichia coli* of Human Origin", Infection and Immunity, 1983, pp. 273-283, vol. 40, No. 1.
International Search Report and Written Opinion from related International Application No. PCT/IB2016/051674, dated Jun. 28, 2016, 12 pgs.
Irizarry et al., "Summaries of Affymetrix GeneChip probe level data", Nucleic Acids Research, 2003, e15, pp. 1-8, vol. 31, No. 4.
Juang et al., "Lipopolysaccaride Inhibits Virus-mediated Induction of Interferon Genes by Disruption of Nuclear Transport of Interferon Regulatory Factors 3 and 7", The Journal of Biological Chemistry, 1999, pp. 18060-18066, vol. 274, No. 25.
Nielubowicz et al., "Host-pathogen interactions in urinary tract infection", Nature Reviews/Urology, 2010, pp. 430-441, vol. 7.
Puthia et al., "IRF7 inhibition prevents destructive innate immunity—A target for nonantibiotic therapy of bacterial infections", Science Translational Medicine, 2016, 336ra59, pp. 1-12, vol. 8, No. 336.
Sirois et al., "TRAF6 and IRF7 Control HIV Replication in Macrophages", PLoS ONE, 2011, e28125, pp. 1-11, vol. 6, No. 11.
Unterholzner et al., "The interplay between viruses and innate immune signaling: Recent insights and therapeutic opportunities", Biochemical Pharmacology, 2008, pp. 589-602, vol. 75, No. 3.

*Primary Examiner* — Amy H Bowman

(57) ABSTRACT

IRF-7 inhibitors have been found to be useful in the treatment of infections, such as bacterial infections. Suitable inhibitors include siRNA molecules as well as small molecules. The inhibitors may be particularly useful in the treatment of bacterial kidney infection, and especially in the treatment of patients having a genetic susceptibility to acute pyelonephritis.

7 Claims, 18 Drawing Sheets
(18 of 18 Drawing Sheet(s) Filed in Color)
Specification includes a Sequence Listing.

Type I IFN related genes

| Functional groups | | Gene names |
|---|---|---|
| IFN and IFN inducible genes | CFT073 | *GBP2↑, IFIH1↑, IFI16↑, IFI27↑, IFI35↑, IFI44L↑, IFIT2↑, IFIT3↑, IFIT5↑, IFITM1↑, IL24↑, ISG20↑, OAS1↑, OAS2↑, OAS3↑, OASL↑, RSAD2↑, TNFSF10↑* |
| | CFT073+ ABU | *IFNB1↑, IFNE↑, IL15↑* |
| IFN receptors | CFT073 | *DDX58↑* |
| | CFT073+ ABU | *IFNAR1↑, IFNAR2↑, IFNGR2↑* |
| Transcription factors | CFT073 | *IRF2↑, IRF2BP1↓, IRF7↑, STAT1↑, STAT3↑, TRIM24↓, TRIM25↑* |
| | CFT073+ ABU | *MAVS↑* |
| Enzymes and other | CFT073 | *DHX58↑, ISG15↑, MERTK↓, PTPN2↑, TRAFD1↑* |
| | CFT073+ ABU | *CYLD↑* |

Figure 1B

| Granulocyte adhesion pathway | Irf3-/- | Irf7-/- | C57BL/6 |
|---|---|---|---|
| Cytokines, chemokines | | | |
| C-X-C motif chemokine | Cxcl3↑↑, Cxcl1↑, Cxcl2↑, Cxcl12↑, Cxcl10↑, Cxcl13↑, Cx3cl1↑ | Cxcl10↑ | |
| C-C motif chemokine | Ccl6↑, Ccl4↑, Ccl3l1/Ccl3l3↑, Ccl9↑, Ccl8↑, Ccl5↑, Ccl24↑ | Ccl28↓ | Ccl6↑ |
| Interleukin | Il33↑, Il1b↑, Il1rn↑, Il36g↑ | | Il20↑ |
| Chemokine-like factor | Cklf↑ | | |
| Platelet factor 4 | Pf4↑ | | |
| Receptors | | | |
| TNF receptor superfamily | Tnfrsf11b↑, Tnfrsf1a↑, Tnfrsf1b↑ | | |
| N-formyl peptide receptor | Fpr2↑ | | |
| Interleukine-1 receptor | Il1r1↑, Il1r2↑ | | |
| G-CSF receptor | Csk3r↑ | | |
| Junction, adhesion | | | |
| Claudin | Cldn4↑, Cldn8↑, Cldn7↑, Cldn11↑, Cldn3↑, Cldn9↓ | | |
| ICAM/VCAM | Vcam1↑, Icam1↑ | | Vcam1↑ |
| Integrin | Itga3↑, Itgb2↑, Itga↑, Itgb1↑, Itga6↑ | | |
| Selectin | Selr, Selplg↑, Selp↑ | | |
| Heat-shock protein b-1 | Hspb1↑ | | Hspb1↓ |
| Syndecan | Sdc1↑, Sdc2↑ | | |
| Moesin | Msn↑ | Msn↑ | |
| CD31 | Pecam1↑ | | |
| E-selectin ligand | Glg1↑ | | |
| Enzymes, peptidases | | | |
| Matrix metallopeptidase | Mmp3↑, Mmp14↓ | | |
| Guanine nucleotide-binding protein G(i) | Gnai2↑ | | |

Figure 3C

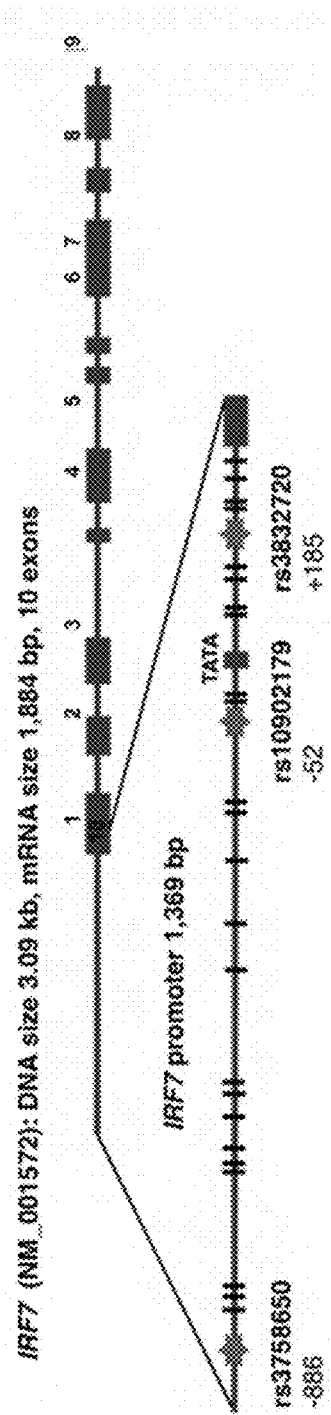
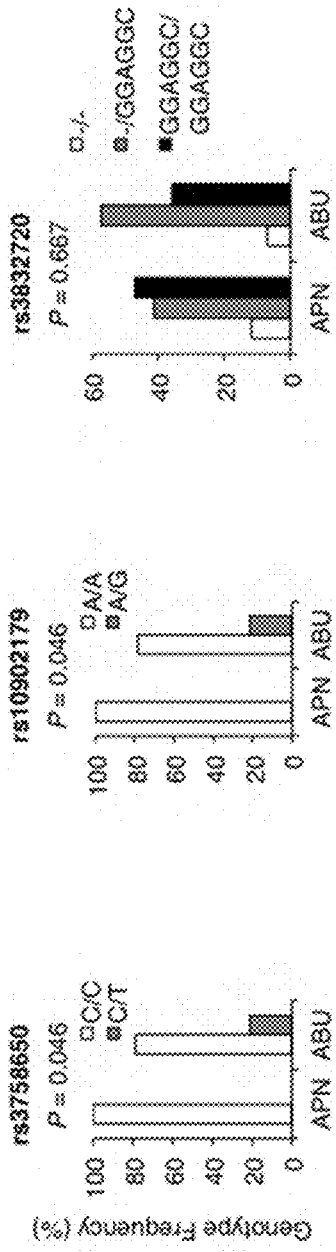
Figure 8A
Figure 8B
Figure 8C

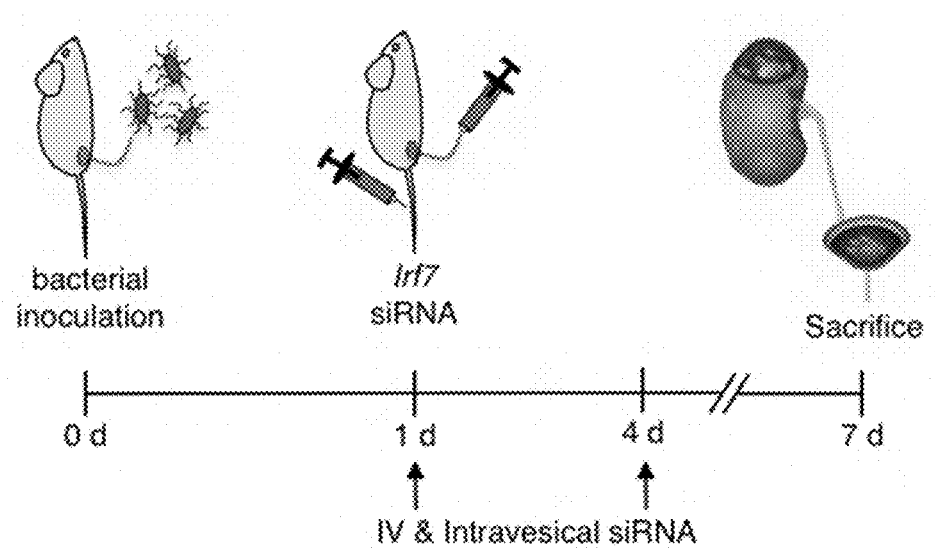
Figure 9A
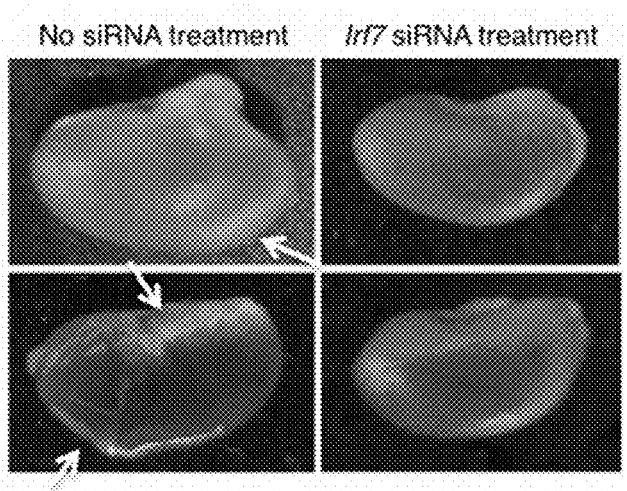
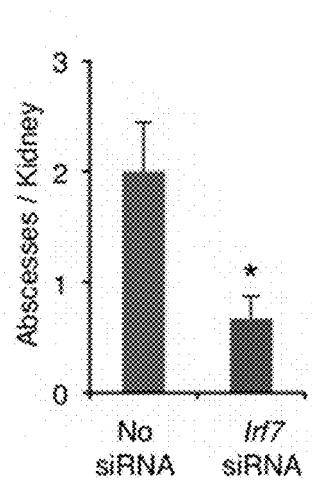
Figure 9B
Figure 9C

THERAPY

The present invention relates to reagents and methods for treating bacterial infections, in particular kidney infections, as well as to pharmaceutical compositions for use in this way.

BACKGROUND OF THE INVENTION

All multicellular organisms need mechanisms for immune recognition, to identify and combat external dangers such as pathogens. The innate immune system protects the host against infection, by eliminating pathogens while sustaining symbiosis with commensals. Innate immunity relies on inflammation to execute the antimicrobial defence, but the response must be carefully balanced, as destructive and protective outcomes may be closely related, and the innate immune response can be a cause of tissue dysfunction and disease. Molecular decisions that distinguish these facets of the immune response are poorly understood, however, which complicates the development of therapies aimed at boosting innate immunity.

Transcription factors regulate the magnitude and flavor of innate immune responses. Transcriptional control of the innate immune response is closely linked to inflammation and antimicrobial effector functions. Innate immunity is also regulated post-transcriptionally and by non-coding RNAs. Interferon regulatory factors (IRFs) control essential aspects of innate and specific immunity. IRF-7, originally identified in the context of Epstein-Barr virus infection, regulates type I interferons (IFNs) and anti-viral responses. In monocytic cells, IRF-3 and IRF-7 form heterodimers and the ratio plays an essential role for the inducible expression of type I IFN genes. Phosphorylated IRF-7 binds together with IRF-3 and NF-κB to virus-responsive IFN-α/β promoter elements and induces low amounts of type I IFNs, which bind to IFNARs and enhance IFN-dependent gene expression.

However, accelerating antibiotic resistance poses a major threat to human health, worldwide. Immunotherapies are therefore emerging as important alternatives to boost the host defense. Immune activation comes with a cost, however, as protective and destructive facets often are activated in concert. There is an obvious need to develop more selective therapies that boost the host defense and prevent pathology. A prerequisite for such developments is to define molecular tools to selectively target destructive inflammation. The applicants studied the effects of transcription factors as they determine the flavor of the innate immune response and in addition to the expression of individual genes.

SUMMARY OF THE INVENTION

The applicants have recently identified IRF3 as an essential determinant of host resistance to Gram-negative bacterial infection. They have now made the surprising observation that Irf7 drives the development of pathology in $Irf3^{-/-}$ mice. The results provide a new molecular context to modulate destructive immune functions in patients with infections, immunodeficiencies or autoimmunity and identify IRF-7 as a means for selective inhibition of pathology caused by bacterial infection.

According to the present invention there is provided an IRF-7 inhibitor for use in the treatment of bacterial infections.

Suitable inhibitors of IRF-7 inhibitor include siRNA molecules, antibodies, small molecule competitors and RNA binding proteins. In particular, the inhibitor of IRF-7 is a siRNA molecule, many of which are available commercially. In an alternative embodiment, the IRF-7 inhibitor is a small molecule competitor, as may be understood in the art. The small molecule competitor may mimic the activity of a siRNA molecule to downregulate expression of IRF-7. Alternatively, it may interact with IRF-7 at the protein level to prevent IRF-7 binding to its natural target. Suitable molecules could be identified by screening as would be understood in the art. In particular, a small molecule is a chemical compound which may be synthetic.

The IRF-7 inhibitor may be used to treat a wide range of infections, in particular because it modifies the immune system and therefore may have both systemic and local effects. The use of IRF-7 inhibitors has been found to be effective in the treatment of bacterial kidney infection or infections of the urinary tract (UTIs) including pyelonephritis, but other infections that may be treated in this way include mucosal infections caused by Gram negative bacteria that activate an Irf7-dependent host response.

Infections that may be treated include any bacterial infections, including gram positive and gram negative infections. Examples include *E. coli* and other members of the Enterobacteriaceae.

In particular, the IRF-7 inhibitor may be used to treat patient having a genetic susceptibility to acute pyelonephritis, as exemplified below.

Candidate genes responsible for pathology were identified by comparative transcriptomic analysis of renal tissues and their expression was verified in infected human cells and patients with acute pyelonephritis, who carried IRF7 promoter sequence polymorphisms associated with high activity. The results demonstrate that beneficial aspects of the host response can be distinguished from destructive forces at the level of individual transcription factors and identify IRF-3 and IRF-7 as essential and opposing immune response regulators, differentially controlling destructive or protective facets of innate immunity.

For administration to patients, the IRF-7 inhibitor is suitably administered in the form of a pharmaceutical composition, which further comprise a pharmaceutically acceptable carrier. Such compositions are known in the art.

Suitable pharmaceutical compositions will be in either solid or liquid form. They may be adapted for administration by any convenient route, such as parenteral, oral or topical administration or for administration by inhalation or insufflation. The pharmaceutical acceptable carrier may include diluents or excipients which are physiologically tolerable and compatible with the active ingredient.

Parenteral compositions are prepared for injection, for example either subcutaneously or intravenously. They may be liquid solutions or suspensions, or they may be in the form of a solid that is suitable for solution in, or suspension in, liquid prior to injection. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

Oral formulations will be in the form of solids or liquids, and may be solutions, syrups, suspensions, tablets, pills, capsules, sustained-release formulations, or powders. Oral formulations include such normally employed excipients as, for example, pharmaceutical grades of mannitol, lactose, starch, magnesium stearate, sodium saccharin, cellulose, magnesium carbonate, and the like.

Topical formulations will generally take the form of suppositories or intranasal aerosols. For suppositories, traditional binders and excipients may include, for example, polyalkylene glycols or triglycerides; such suppositories may be formed from mixtures containing the active ingredient.

The amount of reagent administered will vary depending upon factors such as the nature of the reagent being used, the size and health of the patient, the nature of the condition being treated etc. in accordance with normal clinical practice. Typically, a dosage in the range of from 1 µg-50 mg/Kg for instance from 2-20 mg/Kg, such as from 5-15 mg/Kg would be expected to produce a suitable effect.

In a further aspect, the invention provides a method for treating bacterial infections, said method comprising administering to a patient in need thereof, an effective amount of an IRF-7 inhibitor. Suitable IRF-7 inhibitors are listed above, as are infections that may suitably be treated in this way. Suitable patients include adults and children, and in particular are those who have a genetic susceptibility to infection, for example as a result of a polymorphism in the Irf7 promoter sequence.

Any therapy would suitably be temporary or not long-term, for example, for from 10-28 days, or until the bacterial infection has been cleared, to avoid any potential side effects, such as increased susceptibility to viral infections (an effect noticed in Irf7$^{-/-}$ mice). This would therefore be analogous to current antibiotic therapy, which is administered for a limited time only.

As illustrated below, the applicants have identified the closely related transcription factors IRF-3 and IRF-7 as key regulators of the innate immune response to kidney infection, with opposing effects. Irf3$^{-/-}$ mice developed acute septic infection and extensive pathology but Irf7$^{-/-}$ mice were protected from tissue damage. Transcriptomic analysis identified a network of Irf7-dependent pathology-associated genes in Irf3$^{-/-}$ mice, including, Tlr4, Stat3, Fos and Jun demonstrating that active reprogramming of the host transcriptional machinery accompanies the destructive response in these mice. Human disease relevance was supported by IRF7 promoter sequence variants in pyelonephritis-prone patients and the pathology-associated genes were expressed in patients at the onset of acute pyelonephritis. Importantly, protection of Irf3$^{-/-}$ mice by anti-Irf7 siRNA therapy confirmed the importance of IRF7 as a target for intervention against pathology.

Individual transcription factors have not previously been shown to distinguish beneficial from destructive aspects of innate immunity. Three classes of transcription factors have been proposed to coordinately regulate innate immunity and inflammation, through multiple gene sets that, in turn, control transcriptional "modules" or functional programs, exemplified here by the gene networks and canonical pathways. IRF-3 and NF-κB are examples of Class I transcription factors, which are constitutively expressed, activated by post-translational modifications and responsible for the initial phase of innate immune activation. IRF-7, in contrast, fits into the Class II category of transcription factors, which are synthesized de novo, regulate subsequent waves of gene expression and in some cases, stably reprogram host gene expression. This category also includes different C/EBP isoforms, which are close relatives of c-Fos and c-Jun, which were identified as strong nodes in the pathology associated gene network. The C/EBPs may also interact with CREB and NF-κB, which are central players in signaling downstream of TLR4 in *E. coli*-infected cells. The results suggest that in the absence of Irf3, Irf7 emerges as the predominant transcriptional regulator, with detrimental results for the organism.

In view of reported similarities between IRF-3 and IRF-7, the applicants finding of opposing effects in vivo, in the kidneys of infected mice is surprising. IRF-7 has mainly been studied as a determinant of host resistance to viral infection. Irf7$^{-/-}$ mice respond poorly to hepatitis C and type I IFN responses are reduced. Viral pathogens trigger IRF-7 phosphorylation, nuclear translocation and the formation of a transcriptional complex on the IFN-gene family promoter, together with e.g. NF-κB, c-Jun, activating transcription factor (ATF) 2 and p300/CREB-binding protein. In addition to the convergent regulation by IRF-3 and IRF-7 of anti-viral type 1 IFN responses, the applicants show that IRF-7 regulates a facet of the anti-bacterial response that causes pathology. The reduction in mucosal IRF7 expression by siRNA protected against pathology in susceptible Irf3$^{-/-}$ mice. Controlling this IRF-7 dependent response may be especially important to regulate the anti-bacterial response in the mucosa, where bacteria first contact host cells.

The potential of IRF-7 as a human disease susceptibility determinant was first examined in human kidney cells, where infection activated nuclear translocation and IRF7-dependent gene expression. Remarkably, IRF-7 was also expressed at the time of disease in a patient, who developed acute pyelonephritis. This patient showed massive activation of the IRF7-dependent genes in the pathology-associated network at the time of symptoms. Further evidence of human relevance was obtained by DNA sequencing. IRF7 polymorphisms have previously been associated with the severity of chronic hepatitis C associated liver cirrhosis and IRF7 variants influence the IFN-response in HIV-1 patients. IRF7 genomic region polymorphisms or dysregulated IRF7 expression has been described in SLE patients and a strong connection between SLE and the SNP rs4963128, 23 kb telomeric to IRF7 was found in a GWAS study. IRF7 genomic region polymorphisms are also associated with anti-centromere autoantibody levels in patients with systemic sclerosis. The absence of attenuating IRF7 promoter polymorphisms was identified in APN patients, who developed recurrent episodes of acute pyelonephritis and renal damage during long-term follow up.

DETAILED DESCRIPTION OF THE INVENTION

Transcriptional control of innate immunity was examined in the context of urinary tract infection (UTI)—a high-resolution infection model of an extremely prevalent disease and rapidly emerging antibiotic resistance disaster. The invention will now be particularly described by way of example with reference to the accompanying diagrammatic drawings which are described as follows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A-B. Gene expression in infected human kidney epithelial cells.

FIG. 1A Heat map of Type1 IFN-related genes regulated by CFT073 compared to the ABU strain *E. coli* 83972. FIG. 1B Type I IFN response to CFT073.

FIG. 2A Increased frequency of abscesses in Irf3$^{-/-}$ compared to Irf7$^{-/-}$ and C57BL/6 WT mice. FIG. 2B Bacterial growth and neutrophil infiltration in Irf3$^{-/-}$ compared to Irf7$^{-/-}$ and C57BL/6 WT mice. (Geometric means±SEMs of two experiments, *p<0.05, p<0.01, *p<0.001, 2 way ANOVA). FIG. 2C Bacterial infection was accompanied by massive neutrophil accumulation in the kidneys of Irf3$^{-/-}$ mice (visualized by immunohistochemistry and H&E staining). Irf7$^{-/-}$ mice were protected from tissue damage. Bacterial and neutrophil numbers were low. C57BL/6 WT mice showed moderate pathology, bacterial counts and neutrophil recruitment. Arrows indicate neutrophils.

FIG. 3A-C. Gene expression profiles in infected kidneys from C57BL/6 WT, Irf3$^{-/-}$ and Irf7$^{-/-}$ mice. FIG. 3A Heat map identifying genes regulated by infection in susceptible Irf3$^{-/-}$ mice (7 days post infection, n=4 mice per group). FIG. 3B Pathology-associated IRFs, chemokine- and chemokine receptors genes, transcriptional regulators, innate and specific immunity regulators. FIG. 3C Pathology-specific, IRF7-driven gene network in Irf3$^{-/-}$ mice but not in Irf7$^{-/-}$ or C57BL/6 WT mice, based on direct and indirect interactions between the proteins encoded by those genes.

FIG. 4A Heat map showing the regulation of genes known to interact with IRF-3, IRF-7 and/or IFN-β. FIG. 4B Gene subset exclusive for Irf3$^{-/-}$ and Ifnb1$^{-/-}$ mice.

FIG. 5A Intravenous and intravesical delivery of Irf7 siRNA to susceptible Irf3$^{-/-}$ mice, three days prior to infection and on the day of intravesical infection with *E. coli* CFT073. FIG. 5B Reduction in gross kidney pathology in mice receiving Irf7 siRNA compared to mice receiving scrambled siRNA or untreated controls (7 days after infection, abscesses indicated by arrows). FIG. 5C Immunohistochemistry of frozen kidney tissue sections obtained 7 days after infection. Left panels: Inhibition of mucosal IRF-7 expression in the renal pelvic mucosa of siRNA treated mice. Submucosal STAT3 staining was inhibited, confirming the IRF7-dependence of the STAT3 response. Right panels: Irf7 siRNA markedly reduced bacterial and neutrophil staining, compared to negative control siRNA treated- or untreated Irf3$^{-/-}$ mice. Scale bars are 100 μm. FIG. 5D Irf7 siRNA reduced the frequency of abscesses in Irf3$^{-/-}$ mice but negative control siRNA had no significant effect (n=3-8). Irf7 siRNA also improved bacterial clearance, resulting in lower bacterial counts in urine and renal tissue and reduced the inflammatory response, quantified as neutrophil numbers in urine (means±s.e.m., **P<0.01 by 2 way ANOVA). FIG. 5E Whole genome transcriptomic analysis of kidneys from Irf7 siRNA treated mice, compared to untreated controls, infected with CFT073. The expression of pro-inflammatory genes and transcriptional regulators was suppressed in mice treated with Irf7 siRNA, including chemokines and the pathology network genes Irf7, Stat3 and Jun. Tlr4 was activated, consistent with a fully functional antibacterial defense.

Confocal imaging of IRF7 in human kidney epithelial cells infected with CFT073. Increased cytoplasmic- and nuclear IRF-7 staining, compared to uninfected cells. Scale bars: 20 μm.

Figure 7A:
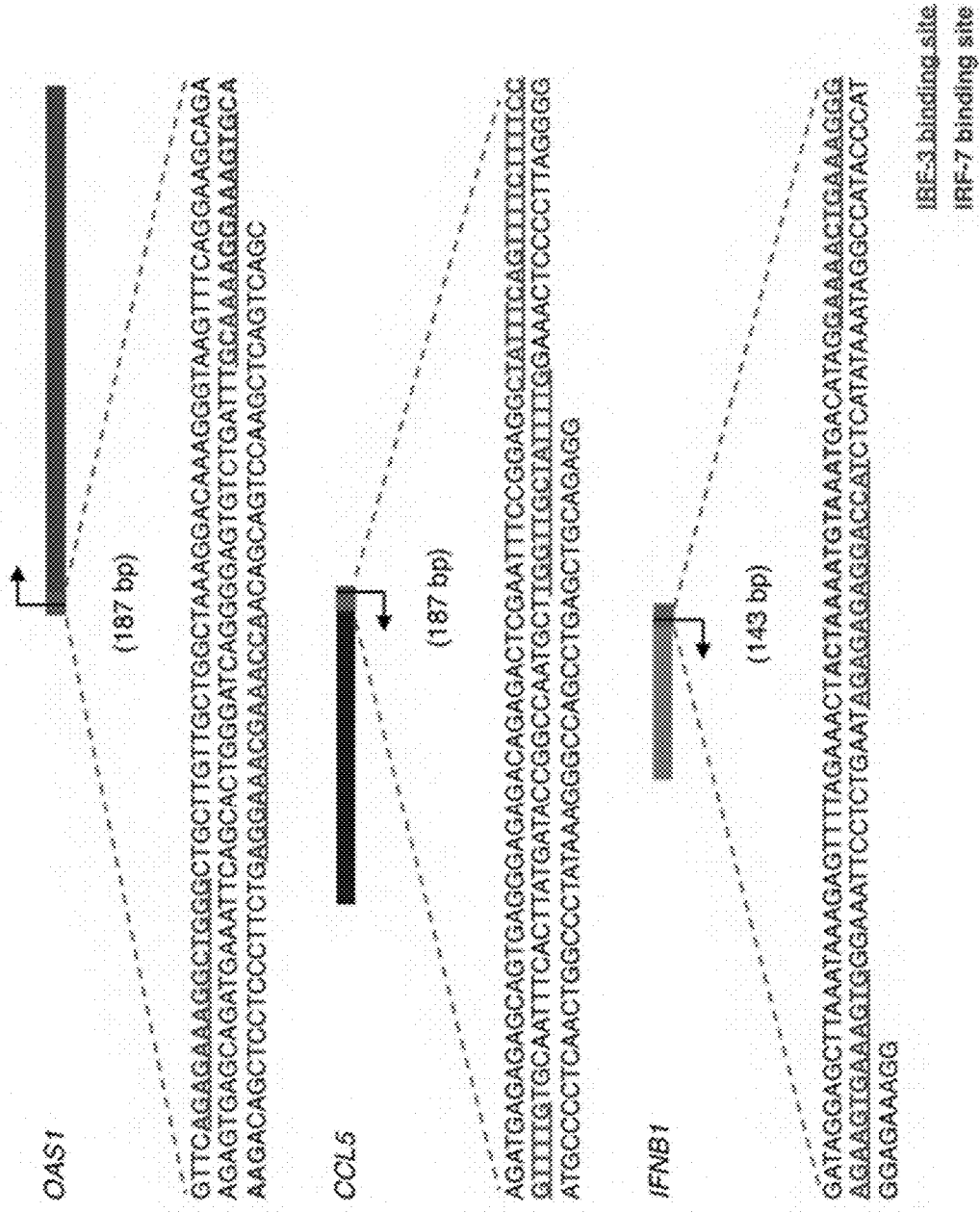
Figures 7B, 7C:
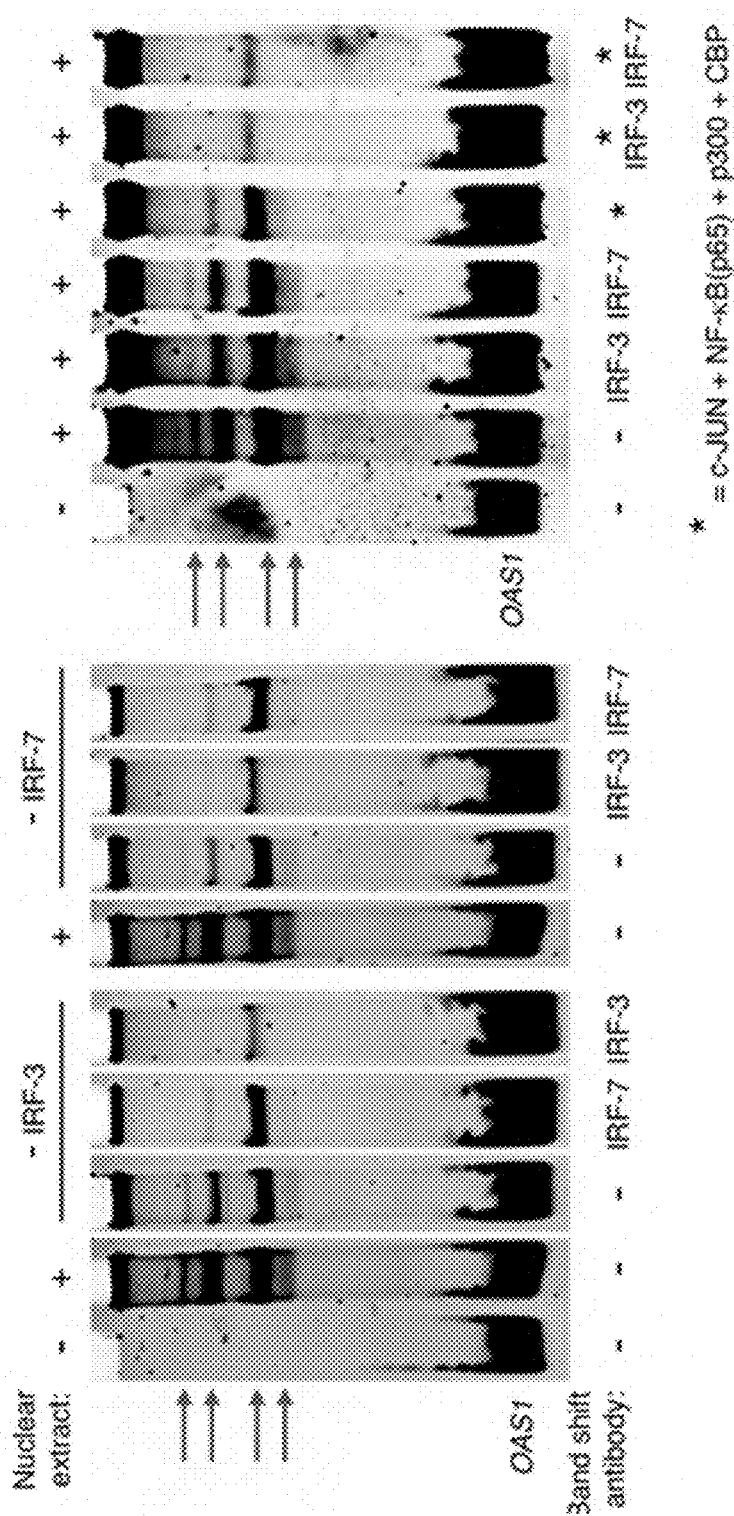

FIG. 7A-C. IRF-3 and IRF-7 binding to OAS1, CCL5 and IFNB1 promoters.

FIG. 7A OAS1, CCL5 and IFNB1 promoter sequences (SEQ ID NOS 3, 4 and 5 respectively). Binding sites for IRF-3 (underlined) and IRF-7 were identified using the JASPAR database. The indicated DNA sequences were amplified by PCR and used for EMSA. FIG. 7B EMSA with the OAS1 promoter oligonucleotide and the nuclear protein extract from kidney cells infected with CFT073. Four different protein-DNA complexes with IRF-3 and/or IRF-7 were detected (arrows). Specificity was confirmed by competitive inhibition with anti-IRF-3 and anti-IRF-7 antibodies and by depletion of IRF-3 or IRF-7 by co-immunoprecipitation. FIG. 7C Binding of IRF-3 and IRF-7 was competitively inhibited by antibodies to other protein partners of in the transcriptional complex (anti-c-JUN, anti-NF-B p65, anti-p300 and anti-CBP antibodies).

Figure 8D:
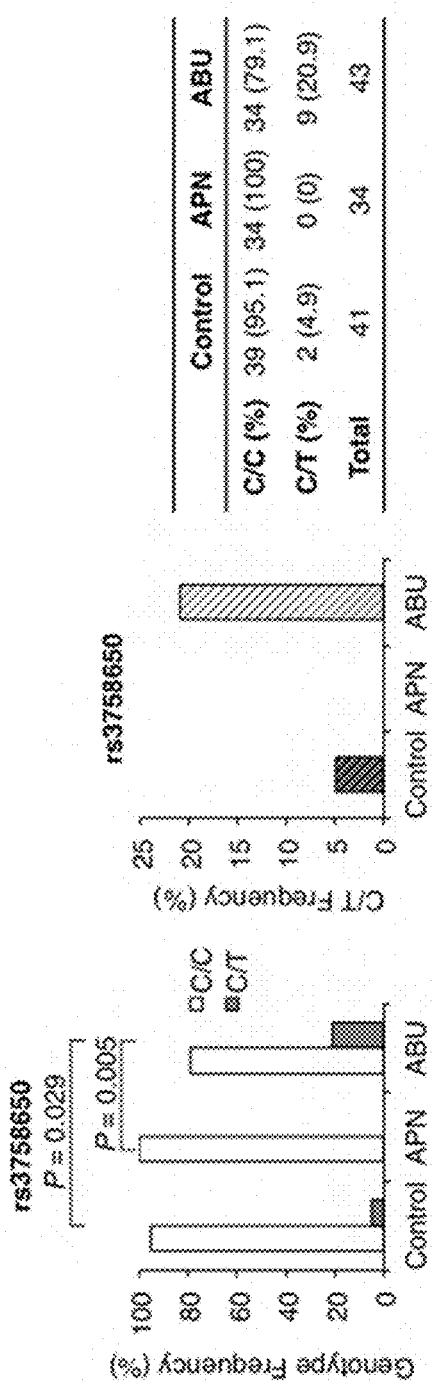
Figure 8E:
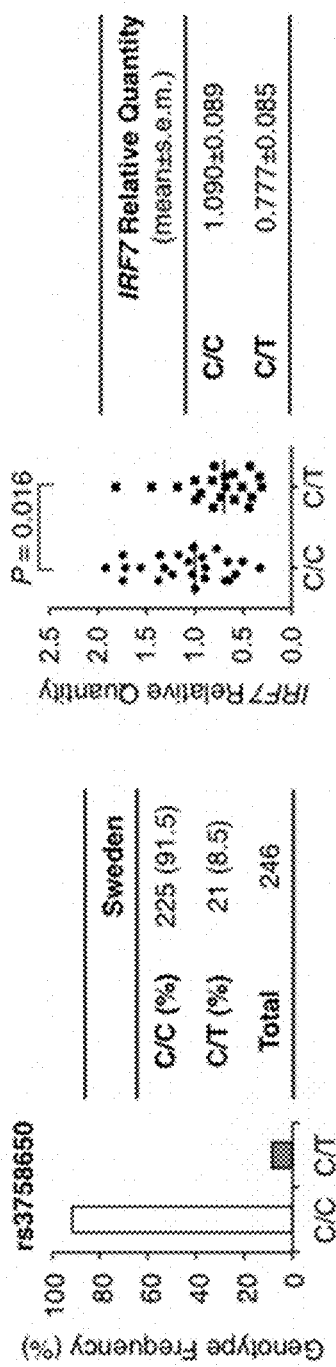

FIG. 8A-E. Human IRF7 promoter polymorphisms associate with lower IRF7 expression and protection against recurrent APN. FIG. 8A Identification of candidate markers. In a total of 31 samples from children with recurrent APN (n=17) or ABU (n=14), three polymorphic SNPs were identified in the IRF7 promoter region (star). Other previously reported SNPs in this region (black line) were not polymorphic in our samples. FIG. 8B Analysis of blood gene expression profiles from 8,086 genotyped Europeans predicted that the rs3758650 minor allele associates with lower IRF7 expression. A similar association was observed in a set of 973 individuals from the Icelandic population. These observations are consistent with the mouse experiments. FIG. 8C For the tightly linked SNPs rs3758650 and rs10902179 ($r^2/d'=1$), the minor allele was exclusively observed among children with the protected ABU phenotype (n=14), whereas all children with the susceptible APN phenotype (n=17) were homozygous for the major allele (Fisher's exact test P-values). FIG. 8D Replication of the over-representation of the rs3758650 minor allele among 43 children with ABU, as compared to 34 children with APN and 41 random blood donors by pyrosequencing (Chi-square test P-values). FIG. 8E Replication of the association between the rs3758650 minor allele genotype (pyrosequencing, n=246) and lower IRF7 expression (qRT-PCR, n=44) in Swedish blood donors ($2^{-\Delta\Delta ct}$ levels with geometric means; two-tailed t-test P-values).

Figure 9D:
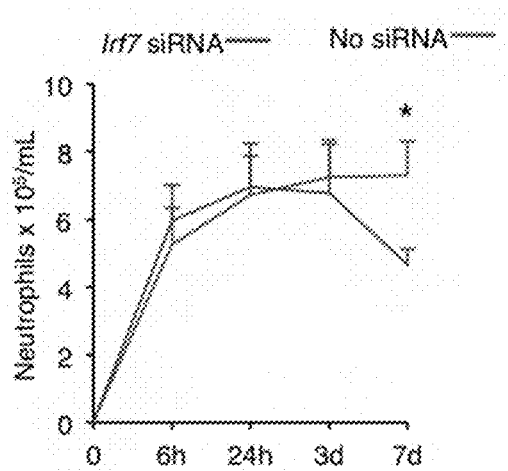
Figure 9E:
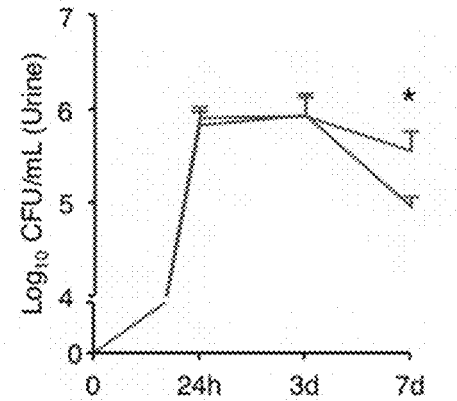

FIG. 9A-E illustrates the efficacy of Irf7 siRNA treatment in APN-susceptible Irf3$^{-/-}$ mice: FIG. 9A shows the siRNA treatment scheme; FIG. 9B shows the kidney pathology of mice treated with Irf7 compared to untreated controls 7 days after infection, with abscesses indicated by arrows: FIG. 9C is a graph illustrating how Irf7 siRNA reduced the frequency of abscesses in Irf3$^{-/-}$ mice; FIG. 9D shows how Irf7 siRNA therapy resolved inflammation, quantified as reduced neutrophil numbers in urine; FIG. 9E shows how Irf7 siRNA treatment also improved bacterial clearance, resulting in lower bacterial counts in urine (n-6 mice per group, means±s.e.m., *P<0.05, unpaired t-test.

Figure 10A:
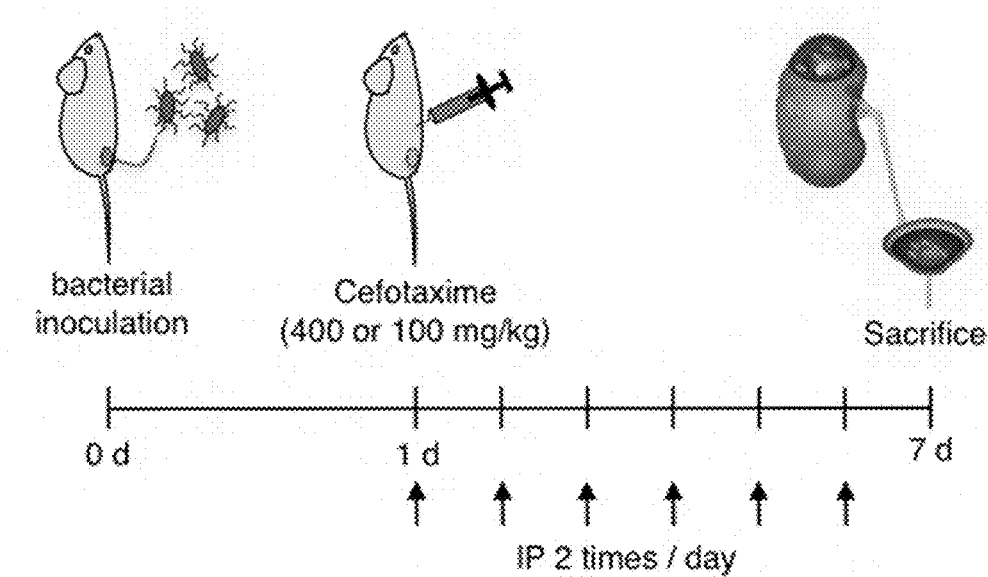
Figure 10B:
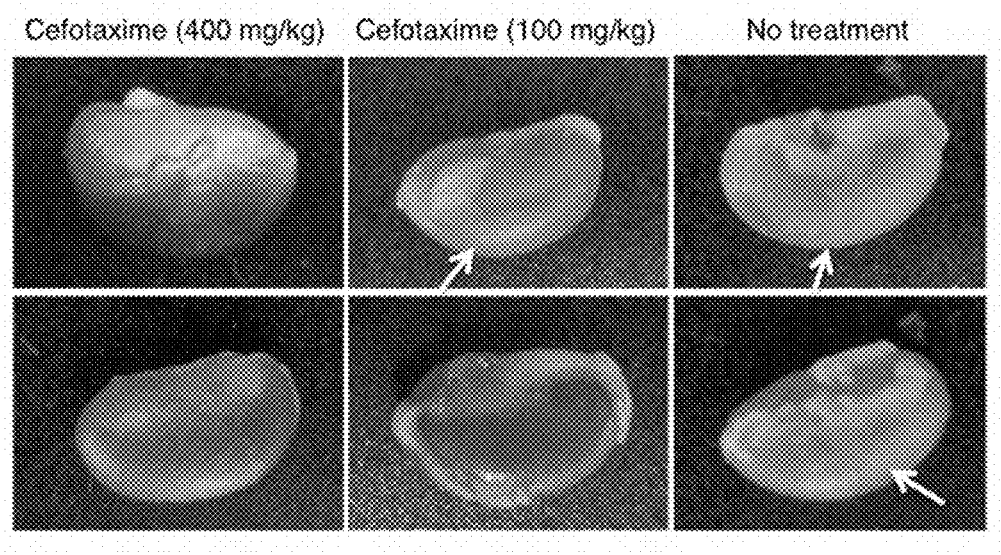
Figure 10C:
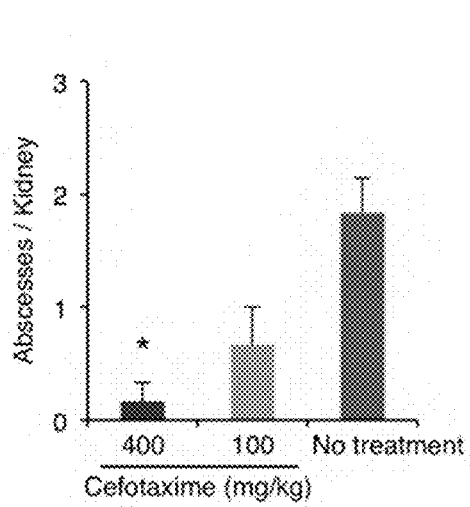
Figure 10D:
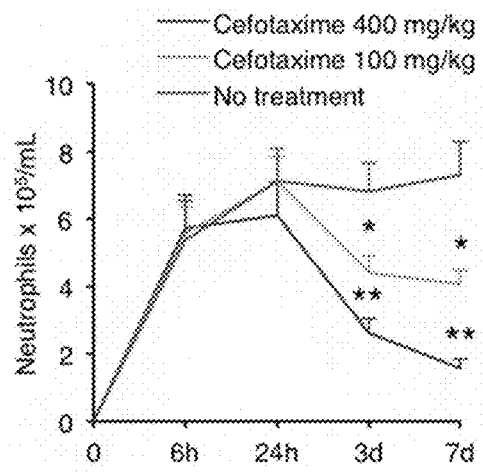

FIG. 10A-D illustrates the comparative efficacy of antibiotic treatment of APN-susceptible Irf3$^{-/-}$ mice: FIG. 10A shows the antibiotic treatment scheme; FIG. 10B shows the kidney pathology of mice treated with Cefotaxime compared to untreated controls 7 days after infection, with abscesses indicated by arrows: FIG. 10C is a graph illustrating how antibiotic treatment reduced the frequency of abscesses in Irf3$^{-/-}$ mice; FIG. 10D shows how Cefotaxime resolved inflammation, quantified as reduced neutrophil numbers in urine (n-6 mice per group, means±s.e.m., *P<0.05, unpaired t-test.

EXAMPLE 1

Study of Gene Expression in Infected Human Kidney Epithelial Cells

To characterize the molecular basis of pathology, infected human kidney epithelial cells were subjected to genome-wide transcriptomic analysis.

The prototype APN strain *E. coli* CFT073 (O6:K2:H1) (Nielubowicz and Mobley, 2010 Nat Rev Urol 7, 430-441), and ABU strain *E. coli* 83972 (OR:K5:H-) (Agace et al., 1993; The Journal of clinical investigation 92, 780-785), were cultured on tryptic soy agar (TSA) plates (16 hours, 37° C.), harvested in phosphate-buffered saline (PBS, pH 7.2, $10^{10}$ CFU/mL) and diluted as appropriate.

Human Kidney Epithelial Cells

Human kidney carcinoma cells (A498, ATCC HTB44) were cultured in RPMI-1640 supplemented with 1 mM sodium pyruvate, 1 mM non-essential amino acids, gentamycin (50 µg/ml) (GE Healthcare) and 10% fetal bovine serum (FBS) (PAA). The A498 cell line is an established model to study UTI pathogenesis (Hedlund et al., 1996). Cells were cultured overnight at 37° C., 90% humidity and 5% $CO_2$ in 6-well plates (for western blots and RNA preparation), or in 8-well chamber slides (for confocal imaging) (Thermo Fisher Scientific) and exposed to CFT072 bacteria in fresh, serum-free supplemented RPMI.

Confocal Microscopy

Kidney epithelial cells, infected as described above, were incubated with rabbit anti-IRF7 (Abcam), rabbit anti-TLR4 (Santa Cruz), rabbit anti-IL6 (Abcam), mouse anti-STAT3 (Abcam) or goat anti-P-c-Jun (Santa Cruz) primary antibodies (1:50 in 5% FBS/PBS, overnight, 4° C.), followed by secondary anti-rabbit Alexa Fluor 488, anti-mouse Alexa Fluor 568 or anti-goat Fluor Alexa 488 conjugated antibodies (1:200 in 5% FBS and 0.025% Triton-X100/PBS, Invitrogen, 1 hour, room temperature), counterstained with DRAQ-5 (Abcam) and examined using LSM 510 META laser-scanning confocal microscope (Carl Zeiss). Fluorescence was quantified using Photoshop CS5.

Western Blotting

Total proteins obtained from A498 cell lysates were separated by SDS-PAGE (4-12% Bis-Tris gels, Invitrogen), and analyzed with rabbit anti-IRF7 (Abcam), rabbit anti-TLR4 (Santa Cruz) and rabbit anti-GAPDH (Santa Cruz) (1:1,000-1:2,000, 5% milk or BSA) primary antibodies followed by HRP-conjugated secondary anti-rabbit antibodies (1:4,000, 5% milk). Restore Western Blot Stripping Buffer (Pierce) was used as indicated. Band intensities were quantified by ImageJ 1.44p.

Gene Expression in Infected Cells

For qRT-PCR, total RNA was isolated from CFT073-infected A498 cells ($10^9$ CFU/mL, 4 hours) with the RNeasy® Mini Kit (Qiagen) and treated with RNase-free DNase (Qiagen). Complementary DNA was quantified in real time using SYBR® Green (QuantiTect® Primer Assays and PCR Kits, Qiagen) for IRF7, JUN, STAT3, IFNB1, IFIT1, IFIT2, IFIT3, IFITM1, IFIH1, MX1, OAS1, ISG15, IF135, DDX58, TRAF3, MAVS, DHX58, STAT1 and S100A8 or TaqMan® (TaqMan® Gene Expression Assays, Applied Biosystems and QuantiFast® Probe Assay, Qiagen) for TLR4, IL6, TNF and IL8 on a Rotor Gene Q (Qiagen). qRT-PCR reactions were run in biological triplicates and gene expression was quantified using a standard curve.

Figure 1A:
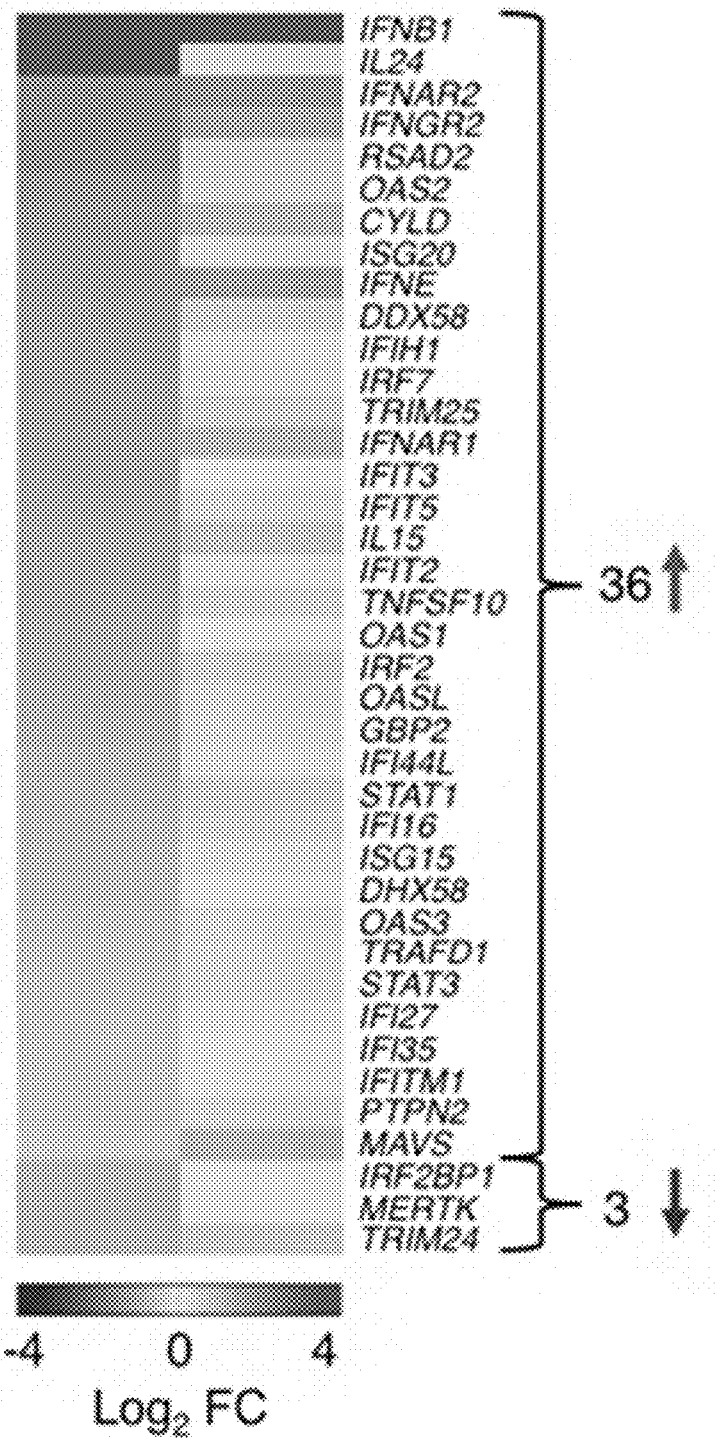

Global gene expression was examined in total RNA extracted by Trizol (Invitrogen) followed by Qiagen RNeasy® clean-up (Qiagen). RNA was reverse-transcribed and converted to biotin-cRNA using TargetAmp Nano-g Biotin-aRNA Labeling kit (Epicentre Biotechnologies), hybridized onto an Illumina Human HT-12 Expression Beadchip for 16 hours at 58° C., washed, stained (Illumina Wash Protocol) and scanned (BeadArray Scanner 500GX). Normalized human kidney cell data was of high quality with replicate correlation >0.98 and no systematic bias. Genes with log 2 fold changes greater than 0.585-fold over buffer control were considered for analysis. Differentially expressed genes were analyzed by Ingenuity Pathway Analysis (IPA) software (Ingenuity Systems, Qiagen). Heatmaps were constructed using the free Gitools 2.1 software. The results are shown in FIG. 1A.

Uropathogenic *E. coli* Trigger a Pathogen-Specific IRF-7 Response

RNA was obtained before and four hours after infection and the pathogen specific response was defined by comparing cells infected with the virulent, uropathogenic *E. coli* strain CFT073 and the virulence-attenuated, asymptomatic bacteriuria (ABU) strain *E. coli* 83972. Significantly altered genes were sorted according to their relative expression levels (empirical Bayes adjusted p-values <0.05 and absolute log 2 fold change >0.585). Affymetrix data was normalized by cross-correlation and found to be of high quality with high replicate correlation (>0.98) and no systematic bias.

The type I IFN pathway was identified as the top scoring canonical pathway in CFT073 infected cells. The pathogen-specific type I IFN response included transcription factors IRF7, IRF2, STAT1 and STAT3, IFNβ1- and effector molecules of the IFN signaling pathway (FIGS. 1A and 1B). IFNs and IFN-inducible genes were activated (n=21), as were IFN receptors (n=4), STAT transcription factors (n=7) and enzymes (n=6). A negative regulator of STAT1 (TRIM24) and a repressor of ATF2-dependent transcription were suppressed (IRF2BP1, IRF2 binding protein 1, potentially enhancing the expression of IFNB1 related genes (FIG. 1B). IRF-3 is constitutively expressed in kidney cells and is activated by phosphorylation in response to *E. coli* CFT073.

IRF7 was identified as an upstream regulator of a CFT073-specific gene network. In addition, NF-κB was a node in this network, mostly downstream of the IRFs. The transcriptional response to CFT073 was verified by RT-PCR, for IFNB1, CXCL8, TNF, STAT1, IRF3, IRF7, IFIT and IFIH genes, OAS1, MAVX, MX, TRAF3, DDX58, DHX58 and S100A8.

The analysis defines a pathogen-specific gene expression profile in human kidney cells, involving IRF3/IRF7, type I IFN-expression and IFN-dependent genes.

The results from the gene expression profiling using Illumina Human HT-12 microarrays as described above revealed an upregulation of pro-inflammatory genes, particularly type I interferon-related genes (FIGS. 1A and 1B). IRF7 expression increased in infected cells and Ingenuity Pathway Analysis (IPA®) showed that genes activated by the pathogenic strain were enriched within the same functional network, implicating IRF-7 as a key regulator of the innate immune response to uropathogenic *E. coli*. Nuclear translocation of IRF-7 was confirmed by confocal imaging of the infected cells. In contrast, the asymptomatic bacteriuria (ABU) strain *E. coli* 83972 did not activate IRF7 expression or trigger nuclear translocation of IRF-7 (data not shown).

EXAMPLE 2

Study of Opposing Roles of Irf3 and Irf7$^{-/-}$ in Pathology and Tissue Damage in Mice.

Experimental Urinary Tract Infection

Mice were bred at the MIG animal facilities, Lund, Sweden. Female C57BL/6 wild type, Ifnb1$^{-/-}$, Irf3$^{-/-}$, Irf7$^{-/-}$, Tlr4$^{-/-}$ mice were used at 9-15 weeks of age. Irf7$^{-/-}$ and Irf3$^{-/-}$ mice were kindly provided by the Riken Bioresource Center, Japan, with permission from T. Taniguchi and Tlr4$^{-/-}$ mice by S. Akira. Ifnb1$^{-/-}$ mice were from F. Ivars, Lund University.

Anesthetized mice (Isofluoran) were infected by intravesical inoculation with *E. coli* CFT073 (108 CFU in 0.1 mL) as described (Hagberg et al., Infection and immunity (1983) 40, 273-283). Overnight static cultures of *E. coli* CFT073 in Luria broth were used for animal inoculations.

Animals were sacrificed after 7 days under anesthesia, kidneys were aseptically removed and macroscopic pathology was documented by photography. Tissues were divided for RNA extraction (on dry ice), histology and immunostaining (in O.C.T. compound, VWR) and frozen in separate vials at −80° C. Infection was assessed by viable counts of homogenized whole kidney (in 5 mL PBS). Urine samples were collected prior to and at regular times after infection and quantitatively cultured. Neutrophil numbers were quantified in uncentrifuged urine by use of a hemocytometer.

Irf3$^{-/-}$ mice developed severe acute pyelonephritis and massive kidney pathology, suggesting that IRF3 controls protective aspects of the host defense.

Histology and Immunohistochemistry

For hematoxylin-eosin staining or immunohistochemistry, tissues embedded and frozen in O.C.T. were cryosectioned (8 μm, Leica microtome). Sections were collected on positively charged microscope slides (Superfrost/Plus; Thermo Fisher Scientific), fixed in acetone-methanol (1:1, 10 min), dried and permeabilized (0.2% Triton X-100, 5% normal goat serum/PBS) and stained with primary rat anti-neutrophil—[NIMP-R14] (1:200; ab2557, Abcam), rabbit polyclonal *E. coli*—(1:100; NB200-579, Novus Biologicals), mouse anti-STAT3—(1:50; ab119352, Abcam) and rabbit anti-IRF7 antibodies (1:100, ab62505, Abcam) and Alexa 488 or Alexa 568 labeled rabbit-anti-rat, goat-anti-mouse and goat-anti-rabbit IgG secondary antibodies (Invitrogen). Nuclei were counterstained with DAPI (0.05 mM; Sigma). Slides were examined by fluorescence microscopy (AX60, Olympus Optical).

Divergent Regulation of APN Susceptibility by IRF-3 and IRF-7

Transcriptional control of in vivo infection by IRF-3 and IRF-7 was evaluated in Irf3$^{-/-}$ or Irf7$^{-/-}$ mice infected with *E. coli* CFT073, compared to C57BL/6 WT mice. The severity of kidney infection was evaluated at sacrifice, 24 hours or seven days after infection and experiments were repeated with at least five mice per group. Urine samples were obtained for culture and immune response analysis after 6 and 24 hours, 3 and 7 days.

Figure 2A:
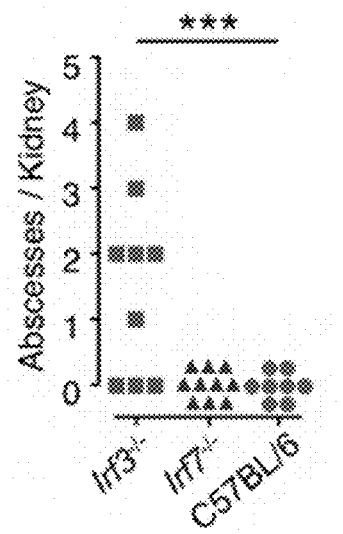
FIG. 2A-C. Opposing roles of Irf3 and Irf7$^{-/-}$ in pathology and tissue damage. Irf3$^{-/-}$, Irf7$^{-/-}$ and C57BL/6 wt mice were intra-vesically inoculated with *E. coli* CFT073 and sacrificed after 7 days.

Major differences in kidney pathology were detected on day seven. Irf3$^{-/-}$ mice developed large macroscopic abscesses, edema and a purulent discharge from the renal pelvis (8/9 mice, FIGS. 2A and 2C). Large areas of tissue disintegration were observed by Hematoxylin-Eosin staining as well as a loss of mucosal integrity and hypertrophy of the renal pelvic epithelium. The pelvic mucosa and renal papilla were infiltrated by neutrophils and urine neutrophil counts increased until day 7. Bacteria crossed the mucosal barriers in the renal pelvis and papilli, following by invasion into collecting ducts and formation of abscesses, specifically micro-abscesses were formed along the renal pelvis (FIG. 2C). In contrast, kidneys of infected Irf7$^{-/-}$ mice remained macroscopically unchanged compared to uninfected mice and in tissue sections the mucosal structure was intact with little or no neutrophil infiltration.

Figure 2B:
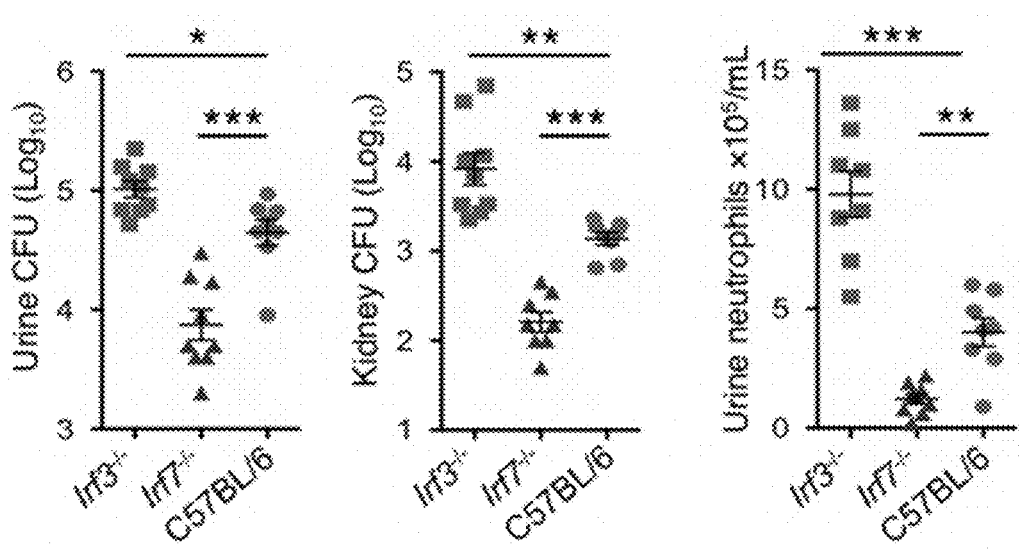
Figure 2C:
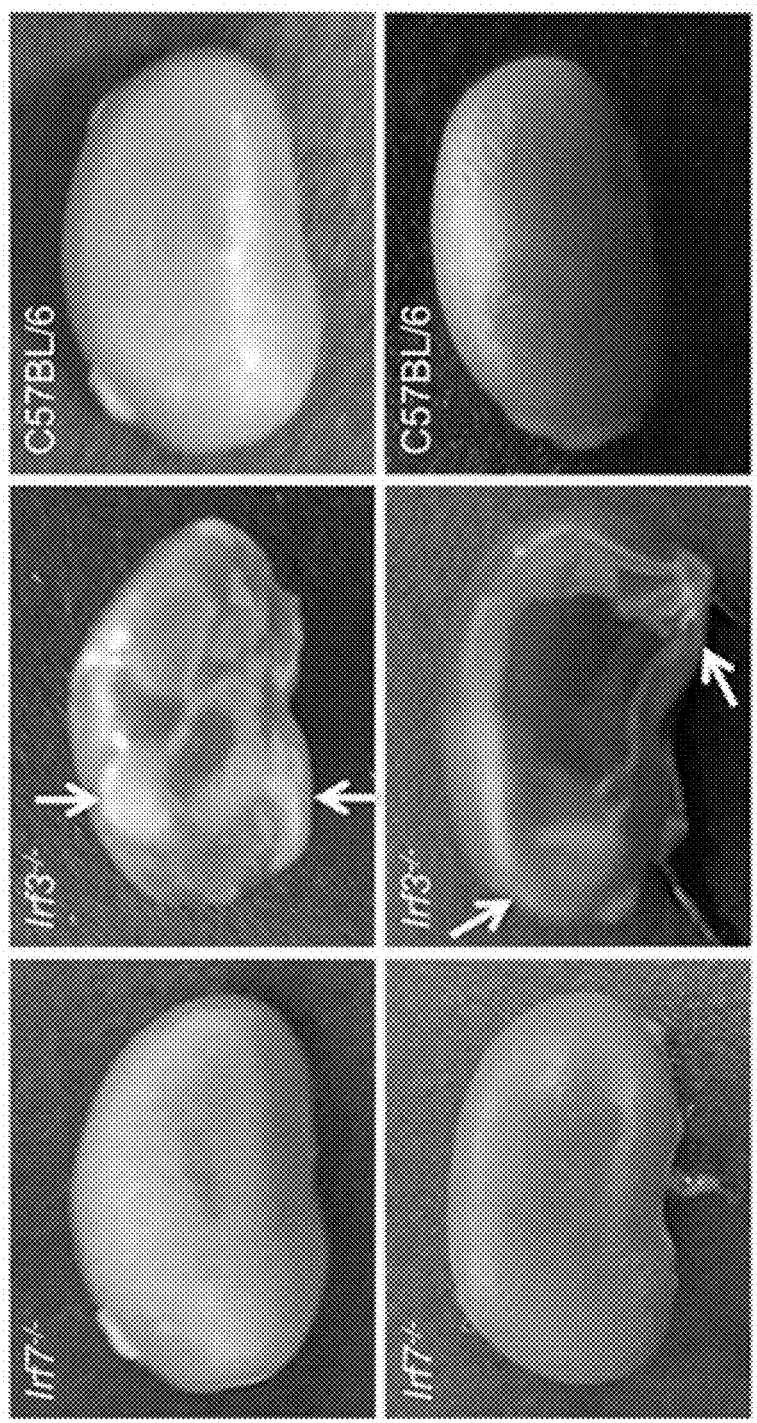

In Irf3$^{-/-}$ mice, bacterial counts increased rapidly during the first 24 hours and continued to increase until day seven (p<0.001 compared to Irf7$^{-/-}$ mice, FIG. 2B). Bacteria were localized by immunohistochemistry in superficial colonies on the surface of renal papilli in Irf3$^{-/-}$ mice after 24 hours with subsequent spread into the collecting ducts and abscesses. Infection showed similar early kinetics in Irf7$^{-/-}$ mice, followed by a rapid decline in bacterial numbers (p<0.001 compared to Irf3$^{-/-}$ mice, urine and kidney counts, on day seven). Superficial bacterial colonies were detected along the pelvic mucosa after 24 hours, but on day seven, bacterial staining was weak). In Irf7$^{-/-}$ mice, urine neutrophil numbers reached an early peak after 24 hours, but then declined to undetectable levels on day seven (p<0.001 compared to Irf3$^{-/-}$, day 7, FIG. 2B).

The surprising differences in disease severity between Irf3$^{-/-}$ and Irf7$^{-/-}$ mice, suggest that the two IRFs control opposing aspects of the innate immune response to infection. While transcriptional control may be maintained by the Irf3/Irf7 heterodimer in WT mice, loss of Irf7 allowed the protective arm of the host response to prevail.

In addition, total kidney RNA was extracted from infected and uninfected mice of each genetic background. After physical disruption in lysis buffer, RNA was extracted with the RNeasy® Mini Kit (Qiagen), amplified using GeneChip 3'IVT Express Kit (Affymetrix), hybridized onto Mouse Genome 430 PM array strips (Affymetrix) (16 hours at 45° C.), washed, stained and scanned in-house using the GeneAtlas® system (Affymetrix). Data was normalized using Robust Multi Average implemented in the Partek Express Software (Bolstad et al., 2003, Bioinformatics 19, 185-1932003; Irizarry et al., 2003, Nucleic acids research, 31, e15). Significantly altered genes were sorted by relative expression (2-way ANOVA model using Method of Moments, p-values <0.05 and absolute fold change >1.41).

The different gene expression profiles in human kidney cells (FIGS. 1A, 1B) suggested that virulence is required to trigger the IRF-7 response. To address this question, we infected Irf3$^{-/-}$ and Irf7$^{-/-}$ mice with the ABU strain *E. coli* 83972 and compared the response to C57BL/6 WT mice. The mice were transiently infected by the ABU strain, with negative cultures on day seven. A low inflammatory response was detected after 24 hours, quantified as urine neutrophil numbers. By seven days, this response had subsided. There was no macroscopic evidence of tissue involvement, defined by lack of edema, hyperemia and abscesses. The results suggest that virulence is required to activate the pathogen-associated IRF-7 signaling pathway.

Pathology-Associated Changes in Gene Expression

Differences in transcriptional control of innate immunity were identified by whole genome transcriptomic analysis of kidney mRNA from Irf3$^{-/-}$ and Irf7$^{-/-}$ mice. Infection-induced changes in gene expression were characterized relative to uninfected mice of each genotype and infected C57BL/6 WT mice served as controls. Affymetrix data was normalized using Robust Multi Average (RMA) implemented in the Partek Express Software (Bolstad et al., Bioinformatics (2003) 19, 185-1932003; Irizarry et al., Nucleic acids research (2003) 31, e15). Significantly altered genes were sorted according to their relative expression levels (2-way ANOVA model using Method of Moments, p-values <0.05 and absolute fold change >1.41).

Figures 3A, 3B:
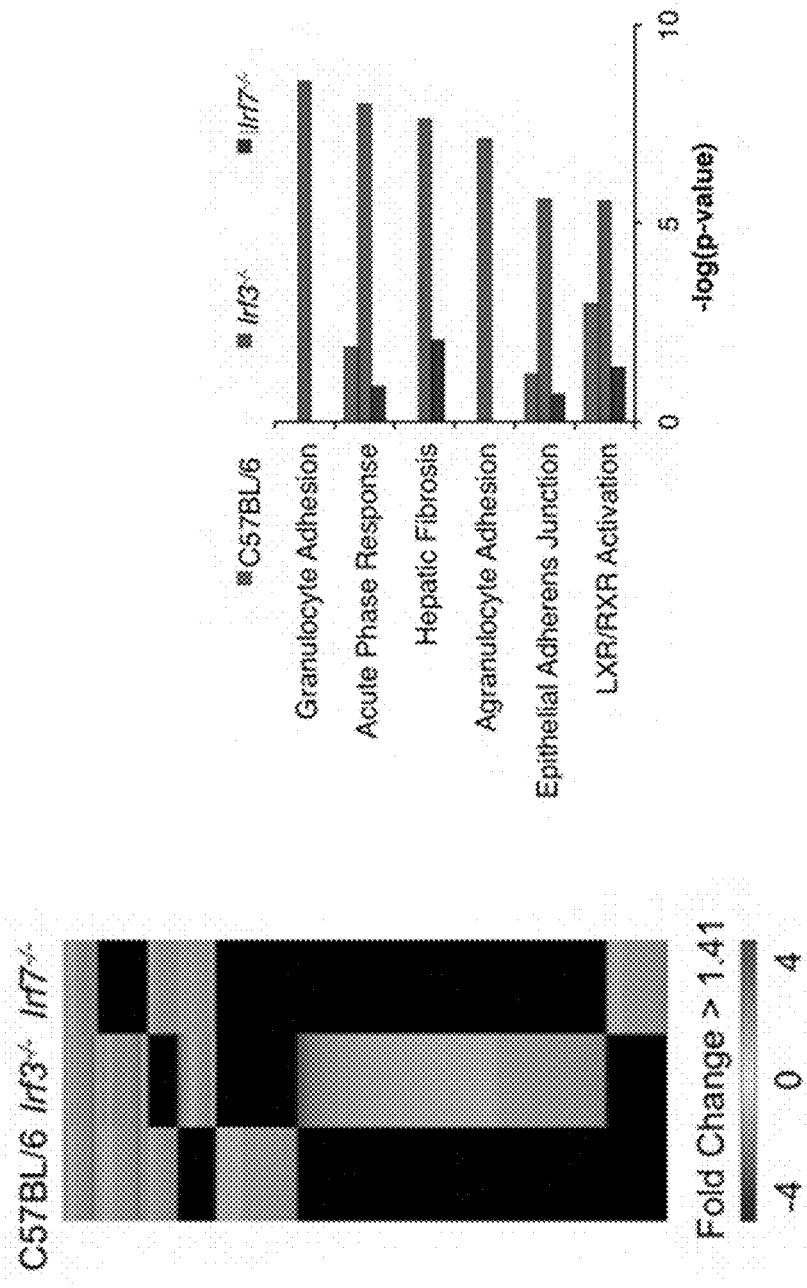

Active reprogramming of the host transcriptional machinery accompanied the development of pathology in Irf3$^{-/-}$ mice (FIG. 3A). Gene expression was activated (956/1,599 genes), especially in mice that developed pathology. The IRF7 gene network observed in human cells was activated in Irf3$^{-/-}$ mice, including NF-κB-, and IFN-induced genes. In contrast, gene expression was mainly suppressed in Irf7$^{-/-}$ mice (400/599 genes) and the IRF7 gene network was not activated.

These results identify IRF7 as an important transcriptional regulator of the pathology-associated response to uropathogenic E. coli.

Qualitative differences in transcriptional regulation were further examined. Major differences in canonical pathway activation between Irf3$^{-/-}$ and Irf7$^{-/-}$ mice were identified by IPA. Consistent with the rapid and sustained neutrophil response in Irf3$^{-/-}$ mice, granulocyte adhesion and migration was identified as a top-scoring pathway (FIG. 3B). Cytokine- and chemokine expression was activated, including Cxcl3 (GRO-3), Cxcl1 (GRO-α), Il33 and Ccl6 (FIG. 3C). The expression of adhesion molecules and ligands was also enhanced as was the expression of TNF receptor superfamily molecules.

The acute phase response pathway was also activated in Irf3$^{-/-}$ mice, including serum amyloid apolipoproteins Saa1 and Saa3, Hp (haptoglobin), C3 (complement factor 3) and TNF-α/IL-1 pathway genes, with Fos as the main activated regulator of downstream gene expression. IL-6 or IFN-β2 is an effector of the acute phase response and an upstream regulator of fibrosis-related molecular targets.

In contrast, these pathways were not significantly regulated in Irf7$^{-/-}$ mice (FIG. 3B), where activated genes were involved in antigen presentation, suggesting a shift from innate to specific immunity in these mice. IFNγ-induced genes were more strongly activated in Irf7$^{-/-}$ mice than in Irf3$^{-/-}$ mice.

These divergent gene expression profiles define the molecular consequences of transcription by Irf3 and Irf7 in infected hosts.

Disease Phenotype in Ifnb1$^{-/-}$ Mice

Since Irf3 and Irf7 both regulate the expression of IFN-β and type I IFN dependent genes, Ifnb1$^{-/-}$ mice were infected with CFT073 and the severity of kidney infection was evaluated after 24 hours or 7 days, as described above. The disease phenotype in Ifnb1$^{-/-}$ mice was similar to that in Irf3$^{-/-}$ mice, with macroscopic renal abscesses and edema. Tissue sections revealed a loss of mucosal integrity, hypertrophy of the renal pelvic epithelium and loss of collecting duct structure. Bacterial and neutrophil numbers increased rapidly in urine and kidneys (p<0.002 and p<0.03, respectively, compared to C57BL/6 controls) and by immunohistochemistry, bacteria were detected in the renal pelvic epithelium, with some evidence of sub-epithelial invasion into the collecting ducts. Neutrophil aggregates were detected along the mucosal barrier, which was severely damaged.

In Ifnb1$^{-/-}$ mice, 866 regulated genes were shared with Irf3$^{-/-}$ mice, as were the top-scoring canonical pathways. TNF-α/IL-1 signaling was more strongly activated in Ifnb1$^{-/-}$ than in Irf3$^{-/-}$ mice, with Fos as the main transcriptional regulator.

These results suggest that IFN-β is an essential effector of the antibacterial response controlled by IRF-3 and a resistance determinant in UTI.

Gene Expression and Tissue Pathology

Figures 4A, 4B:
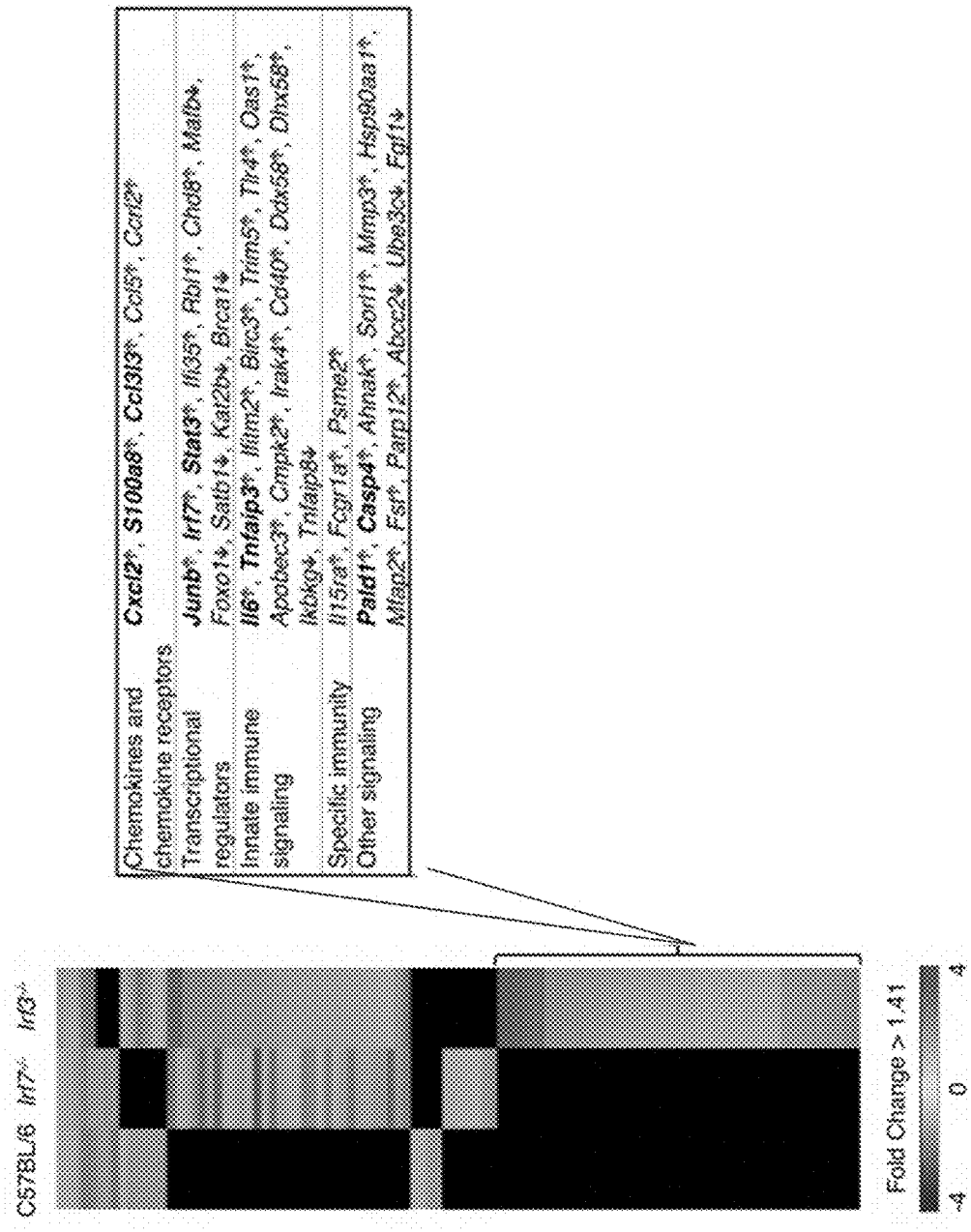
FIG. 4A-B. Target genes associated with severe infection and acute pathology.

To identify genes driving pathology, the data set was probed for molecules that interact with IRF-3, IFN-β and/or IRF-7. The subset of genes regulated exclusively in the Irf3$^{-/-}$ and Ifnb1$^{-/-}$ mice that developed pathology was analyzed further (FIGS. 4A and 4B).

Based on published evidence of direct or indirect molecular interactions, a network was constructed to connect the pathology-associated genes (n=46,). IRF-7, TLR4, IL-6, NFKBIA (IκB-α), c-FOS and STAT3 were identified as major nodes in this network. IRF-7 was predicted to be in direct contact with 25 of the network members, including OAS1 and 2, IRAK-4, DHX58, S100-A8, caspase-4 and TRIM5, plasma membrane localized molecules CCRL2, IgG Fc receptor I (FCGR1), TNF receptor superfamily member 5 (CD40) and IL-15R-α as well as CCL5, which is secreted. In addition, STAT3 connects IRF-7 to nuclear proteins, including Catenin β-1 (CTNNB1), MAD homolog 3 (SMAD3), IFI35, c-Fos, c-Jun and Jun-B, after the Irf7-dependent mucosal activation of cytokines, IFNs, interleukins. C-Fos regulates transcription in conjunction with c-Jun and increased expression of Fos and Junb predicted an increase in activator protein (AP) AP-1-dependent transcription, stimulating the expression of innate immune signaling molecules like Il6 and Tnfaip3, which were strongly enhanced. IL-6 regulates the acute phase response and interacts with SMAD3, Jun-B, c-Fos and NFKBIA. IL-6 expression is, in turn, regulated by STAT3 and c-Jun.

The contribution of c-Fos and c-Jun to pathology was further analyzed as AP 1-dependent gene expression, which was activated in Irf3$^{-/-}$ and Ifnb1$^{-/-}$ mice but not in Irf7$^{-/-}$ mice. In addition, NF-κB-dependent gene expression was specifically activated in Irf3$^{-/-}$ and Ifnb1$^{-/-}$ mice. TLR4, which is a master regulator of innate immunity, was a major node in the pathology network, with 19 interaction partners, including IRF-7. Importantly, the pathology-associated genes were not regulated in infected Tlr4$^{-/-}$ mice and there was no evidence of kidney pathology. The lack of transcriptional regulation in Tlr4$^{-/-}$ mice was confirmed by RT-PCR, compared to uninfected mice, suggesting that TLR4 controls IRF7-dependent pathology.

In vivo support for an Irf7 response to infection was obtained by immunohistochemistry. IRF-7 staining increased markedly in the renal pelvic epithelium of infected Irf3$^{-/-}$ and Ifnb1$^{-/-}$ mice. STAT3 expression was only detected in the submucosa and was absent in Irf7$^{-/-}$ mice confirming that the STAT3 response is Irf7 dependent.

The results identify a pathology associated gene network driven by Irf7 and confirm the expression of IRF7 in tissues from infected mice.

EXAMPLE 3

Figure 5A:
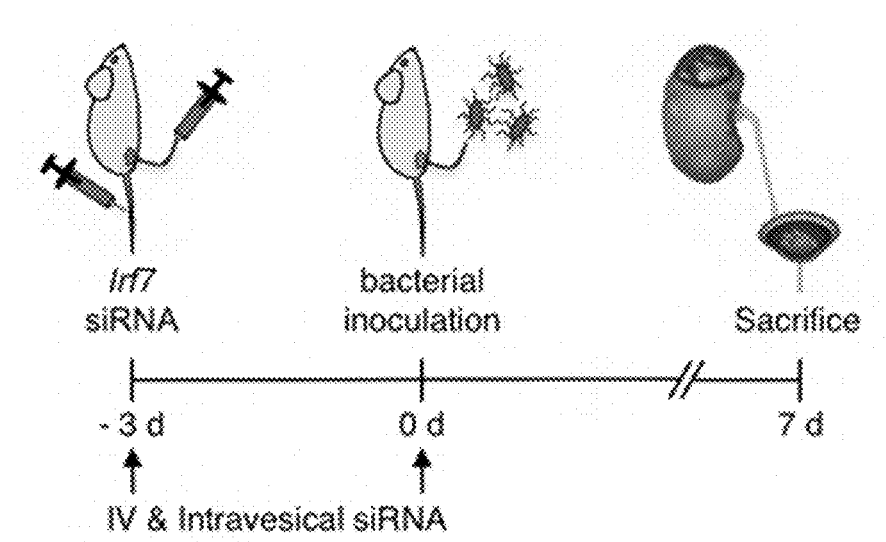
FIG. 5A-E. Protection by liposomal delivery of Irf7 siRNA in susceptible Irf3$^{-/-}$ mice.

In Vivo Inhibition of Irf7 Expression by Specific siRNA Therapy siRNA therapy was used to confirm the role of Irf7 in pathology. Irf3$^{-/-}$ mice were subjected to siRNA treatment at a dose of 5 mg/kg. A dose (300 μL) of Silencer Select Pre-designed Irf7 siRNA (Life Technologies, 4404010 #s79411) was injected into the tail vein (200 μL) and intravesically (100 μL), three days prior to and on the day of infection with Invivofectamine reagent (Life Technologies, 1377501) (FIG. 5A). The siRNA used was as follows:

```
Sense:        GUGUUUACGAGGAACCCUAtt       (SEQ ID NO 1)

Antisense:    UAGGGUUCCUCGUAAACACgg       (SEQ ID NO 2)
```

Ambion In Vivo Negative Control siRNA was given as a control (Life Technologies, 4457287). For transcriptomic analysis, total RNA was isolated from the kidney of Irf3$^{-/-}$ mice using mirVana miRNA Isolation Kit (Ambion by Life Technologies) followed by organic extraction using Acid-Phenol:Chloroform. The analysis was done in-house using Mouse Genome 430 PM array strips and GeneAtlas system (Affymetrix).

Figure 5B:
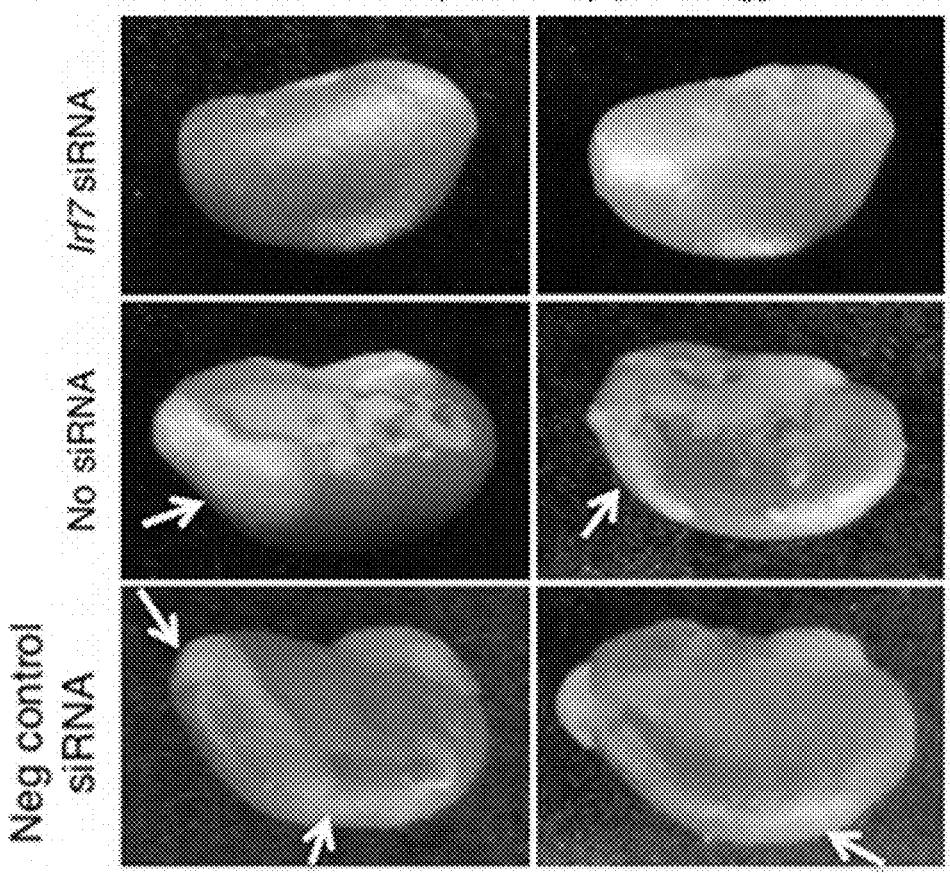

After 7 days following infection, mice were sacrificed. The disease phenotype was defined by macroscopic kidney pathology, number of abscesses, bacterial counts in urine and kidneys, urine neutrophil numbers and tissue imaging (FIGS. 5B and 5D). Irf7 siRNA-treated mice were compared to infected controls receiving irrelevant siRNA with Invivofectamine® or no treatment.

Irf7 siRNA-treated mice showed a reduction in macroscopic kidney pathology and tissue damage, bacterial counts and neutrophil recruitment, compared to infected controls receiving irrelevant siRNA (FIG. 5B). Suppression of Irf7 expression was confirmed in vivo, by mucosal IRF7 staining, also detecting reduced submucosal STAT3 staining. In addition, the expression of proinflammatory genes was suppressed, especially chemokines involved in neutrophil recruitment (FIG. 5D).

Figure 5C:
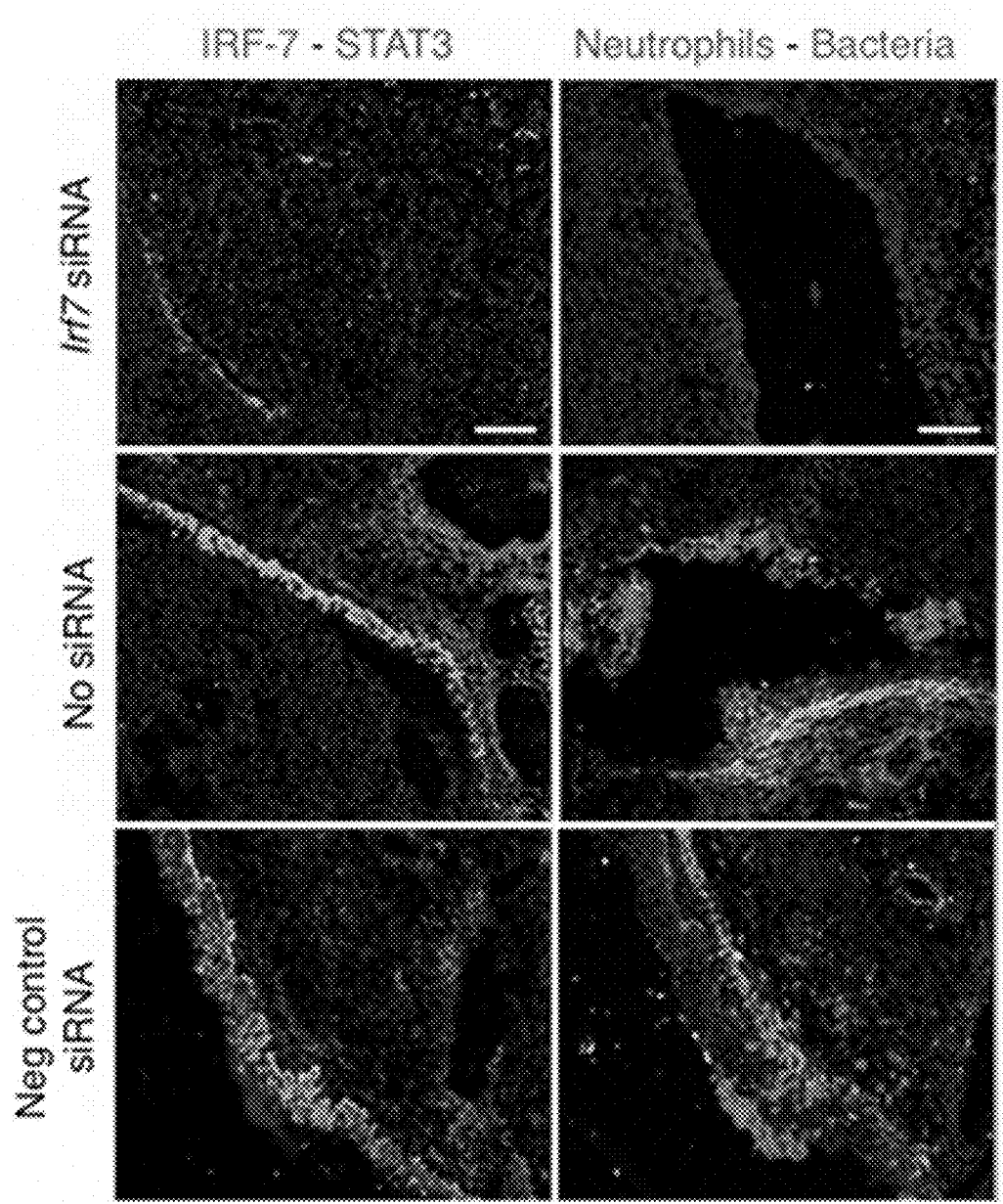
Figure 5D:
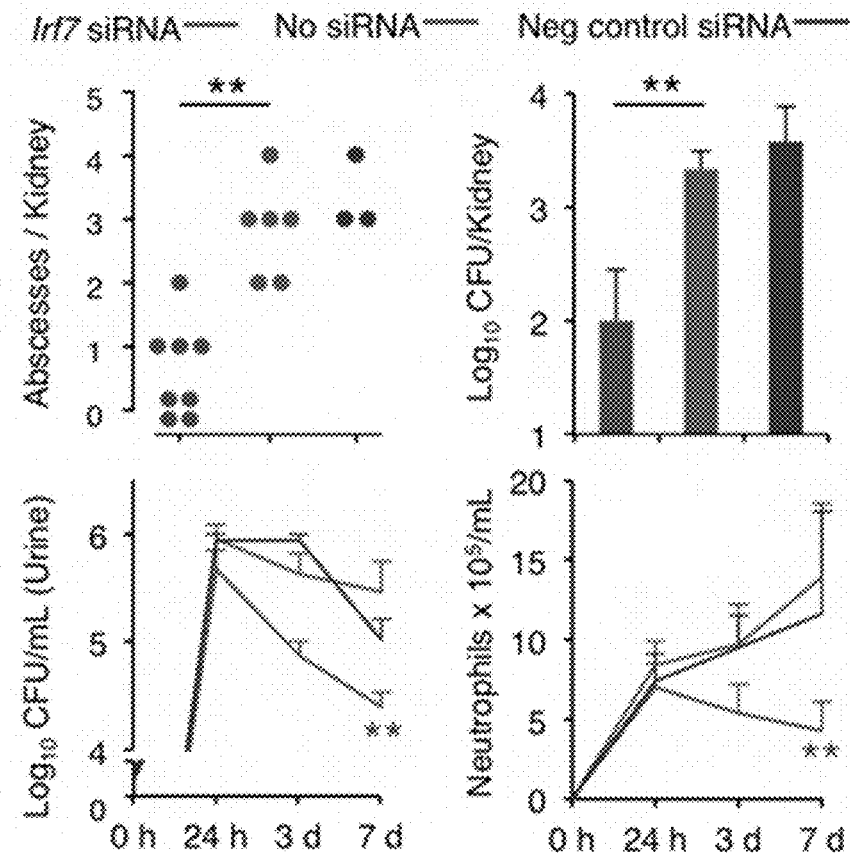
Figure 5E:
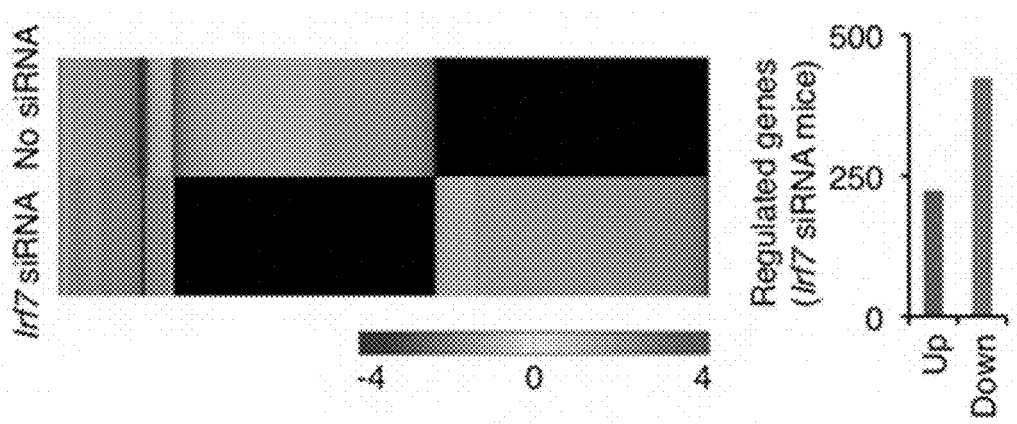

Reduced IRF-7 expression was confirmed by immunohistochemistry, in renal epithelial tissue (FIG. 5C). Furthermore, the transcript levels were overall suppressed and specifically for genes (including Stat3, S100a8, Cxcl2, Junb) which were identified as pathology-associated in infected murine kidney, further supporting that IRF-7 expression is suppressed by siRNA in vivo (FIG. 5E).

The results confirm the role of Irf7 as a transcriptional regulator of pathology and identify Irf7 as an important therapeutic target in attempts to suppress dysregulated innate immune responses and pathology.

EXAMPLE 4

Gene Expression in Patients with UTI

Five patients with recurrent lower UTI and incomplete bladder emptying were inoculated with E. coli 83972 (Sunden). P fimbrial expression was re-established in E. coli 83972 by reconstitution of the pap gene cluster. Blood and urine samples were collected prior to inoculation and repeatedly after inoculation. Patients had access to a direct telephone number to the study physician at all times, and were prescribed antibiotics to be used immediately in case of symptoms as instructed by the physician.

Patient RNA was extracted from peripheral whole blood, purified by QIAamp RNA Blood Mini Kit (Qiagen), amplified using GeneChip 3'IVT Express Kit (Affymetrix) and hybridized using the GeneAtlas system (Affymetrix). Data was normalized using Robust Multi Average (RMA) implemented in the Partek Express Software (Partek). Human in vitro data was pre-processed and normalized using cross-correlation (Chua et al., Nucleic Acids Research (2006) 34, e38).

DNA Amplification and Sequencing in Patients with Recurrent UTI

Genomic DNA was extracted from heparinized peripheral blood of patients with APN, ABU or healthy controls using the QIAamp DNA Blood midi kit (Qiagen) and TrueStart Hot StartTaq mixture (Thermo Fisher Scientific). Sequenced products (GATC biotech), were analyzed by DNAClub (by Xiongfong Chen) and BioEdit 7.0 (by Tom Hall).

IRF7 Promoter Genotyping

The IRF7 promoter SNP (rs3758650) from patients with ABU (n=43), APN (n=34) and controls (n=41) was genotyped using pyrosequencing of chromosomal DNA on a PyroMark 96MA instrument (Qiagen).

Figure 6:
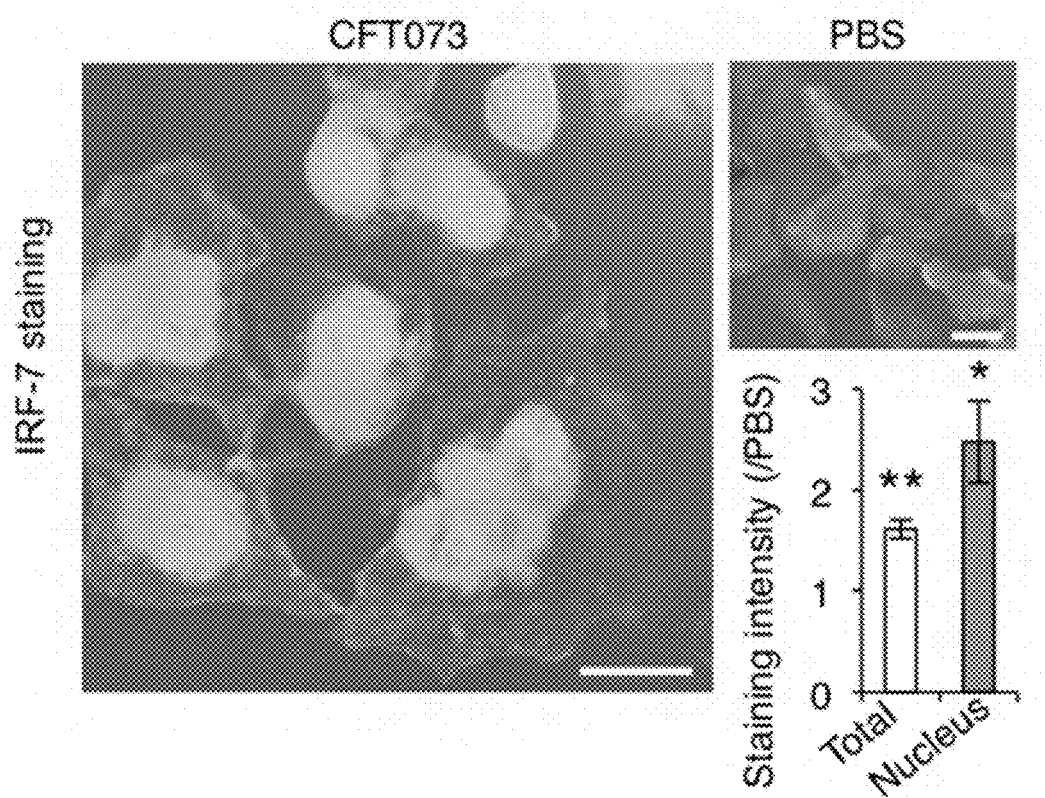
FIG. 6. Human relevance of IRF-7 activation.

Expression of IRF7 and Pathology-Associated Genes in Infected Human Kidney Cells and Infected Patients The expression of IRF-7 and the pathology-associated molecules was examined in vitro, in human kidney cells. CFT073 infection (four hours) activated IRF7 expression, as shown by RT-PCR. By confocal microscopy, a dramatic increase in staining was detected, with nuclear translocation of IRF-7 (FIG. 6). The increase in IRF-7 protein levels was confirmed by Western blots. In addition, infection increased cellular levels of TLR4, IL-6 and phosphorylated c-Jun as well as the expression of IL6 and JUN. TLR4 and STAT3 were not transcriptionally regulated in epithelial cells.

The disease-association of IRF7 expression was further examined by genome-wide transcriptomic analysis of patient mRNA, extracted from peripheral blood leucocytes during ABU and at the onset of symptoms of acute pyelonephritis. A dramatic increase in IRF7 expression was detected at the time of symptoms, compared to the ABU sample from the same patient. In addition, the expression of pathology-associated network genes was massively enhanced at this time. These findings confirm that the response that accompanies acute pyelonephritis includes IRF-7 as well as specific pathology-associated genes.

Promoter Sequence Interactions of IRF3 and IRF7 Demonstrated by EMSA

The applicants examined if both IRF-3 and IRF-7 bind to the promoters of the IRF7-dependent genes that were upregulated in vivo. DNA fragments of 187 bp from the OAS1 and CCL5 promoter and a fragment of 143 bp from the INFB1 promoter were amplified and used as probes in electrophoretic mobility shift assays (EMSAs) (FIG. 7A). Each of the DNA fragments was shown to interact strongly with a nuclear protein extract from kidney cells infected with CFT073, resulting in four band-shifts for the OAS1 and CCL5 promoters and five for the INFB1 promoter (FIG. 7B). The probes alone formed a single low molecular weight band, serving as a negative control. Specificity for IRF-3 and IRF-7 was confirmed by competitive inhibition, using IRF3- or IRF7-specific antibodies and by depletion of IRF-3 or IRF-7, by co-immunoprecipitation with specific antibodies. Depletion was confirmed by Western blots, showing a marked reduction in band intensity (FIG. 7B).

A marked change in IRF-3 and IRF-7 band intensities was detected by EMSA after inhibition of known protein partners in the IRF-3/7 transcription complex or related proteins (e.g. enhanceosome), (FIG. 7C). The c-JUN and NF-κB regulatory kinase IKK-ε was transcriptionally regulated in an IRF7-dependent manner in Irf3$^{-/-}$ mice (FIG. 7C). C-JUN and its cofactor ATF-2, the p65 (RELA) subunit of NF-κB, as well as the CREB binding protein (CBP) and p300 that acetylate IRF-3 assist in IRF-3 activation and nuclear translocation.

The results show that IRF-3 and IRF-7 bind to these promoter sequences both together and independently, suggesting that IRF-7 can regulate these genes also in the absence of IRF-3 and vice versa.

IRF7 Promoter Genotyping in Patients with Urinary Tract Infection

Because of the protective phenotype observed in Irf7$^{-/-}$ mice, we next hypothesized that genetic IRF7 variants might influence the risk for acute pyelonephritis in humans. While analysis of whole-exome sequencing data from a range of individuals showed that IRF7 loss-of-function mutations are exceedingly rare, analysis of blood gene expression data from individuals genotyped using single-nucleotide polymorphism (SNP) microarrays revealed promoter variants associated with altered IRF7 expression. To identify candidate variants, we therefore sequenced the IRF7 promoter region in 17 Swedish children with recurrent APN. Following an initial APN episode, these children were prospectively monitored for a minimum of five years to establish their susceptibility to APN. Additionally, we included 14 children who were diagnosed with ABU, but never developed APN and thus show evidence of a protected phenotype.

In the combined set of samples, we found three polymorphic IRF7 promoter single-nucleotide polymorphisms (SNPs) (rs3758650, rs10902179 and rs3832720; FIG. 8A). Rs3758650 and rs1092179 are tightly linked, common SNPs (MAF 6.9%), annotated as associated with lower IRF7 expression in the eQTL database (FIG. 8B).

Remarkably, all of the children with APN were homozygous for the major allele rs3758650-C, which confers high IRF7 expression. By contrast, a proportion of the children with ABU were heterozygous for rs3758650-T, which confers lower IRF7 expression (Fisher exact test P=0.0463). An identical association was observed for the linked rs10902179 allele, whereas the rare rs3832720 showed no disease association (FIG. 8C). For validation, we genotyped an independent series of children with APN (n=34) or ABU (n=43) plus a series of Swedish blood donors (n=41) (FIG. 8D). Again, the rs3758650-T allele was more common in children with ABU as compared to children with APN or blood donors (Fishers exact test P=0.0045 and P=0.0293, respectively; FIG. 8D). Furthermore, the association between rs3758650-T and reduced IRF7 expression was replicated in Swedish and Icelandic individuals (FIG. 8E). These data demonstrate the existence of common IRF7 variants that protect against recurrent APN in children. We also noted that other IRF7 variants have been associated with viral infections and autoimmune conditions.

These results also identify Irf7 as a target for immunomodulatory therapy in acute pyelonephritis. These findings identify IRF7 inhibition as a non-antibiotic approach to protecting highly susceptible children against recurrent acute pyelonephritis.

EXAMPLE 5

Comparison of Irf7 siRNA Treatment with Antibiotic Therapy

Irf7 siRNA treatment was compared with antibiotic therapy. Groups of 6 Irf3$^{-/-}$ mice were treated intravenously and intravesically with siRNA as described in Example 3, 24 hours and 4 days after intravesical infection with *E. coli* CFT073. The 24 hour time point corresponds to the time of acute symptoms, when patients are first diagnosed with febrile urinary tract infection (UTI) and treatment is initiated.

Also at that time, and following infection with *E. coli* CFT073, Irf3 mice were treated with the third-generation cephalosporin broad-spectrum antibiotic, Cefotaxime (STRAGEN Nordic A/S) at a dose of 100 or 400 mg/kg body weight. Cefotaxime was given by intraperitoneal injection twice a day for 6 days starting 24 hours after infection.

After 7 days, the mice were sacrificed, and kidney pathology and inflammation as quantified by neutrophil numbers in urine was assessed. Bacterial clearance was also assessed in SiRNA treated mice by measuring bacterial counts in urine. The results are shown in FIGS. 9A-E and 10A-D respectively.

SiRNA therapy significantly reduced the disease score as measured by the number of abscesses and the magnitude of the neutrophil infiltrate (FIGS. 9B and 9C). The effect of Irf7 siRNA was similar to 100 mg/kg of Cefotaxime (FIG. 10C) but lower than 400 mg/kg, suggesting that optimization of Irf7 inhibition therapy could result in complete clearance of infection, comparable to the protected phenotype in Irf7$^{-/-}$ mice. This conclusion was supported by the absence of pathology-associated gene expression in Irf7 siRNA treated mice, confirming the mechanistic role of Irf7 in this model.

Statistical Analysis

In the above Examples, pathology, bacterial numbers and neutrophil responses were compared by 2 way ANOVA. Unpaired two-tailed Student's t-test for homoscedastic variances was used to evaluate RT-PCR data using InStat software (v. 3.06, GraphPad). Two-tailed Chi-square test was used to evaluate the genotyping data. In all cases p-values <0.05 were considered significant. Data was examined in Prism (v. 6.02, GraphPad).

The invention claimed is:

1. A method for the treatment of an infection, said method comprising administering to a patient in need thereof, an effective amount of an IRF-7 inhibitor, wherein the infection is an Enterobacteriaceae infection.

2. The method of claim 1, wherein the IRF-7 inhibitor is a siRNA molecule or a small molecule.

3. The method of claim 1, wherein the IRF-7 inhibitor is administered in the form of a pharmaceutical composition.

4. The method of claim 1 wherein the Enterobacteriaceae infection is an Enterobacteriaceae kidney infection.

5. The method of claim 1 wherein the patient has a genetic susceptibility to acute pyelonephritis.

6. The method of claim 5 wherein the genetic susceptibility is due to a polymorphism in the promoter sequence of IRF7.

7. The method of claim 6 wherein the polymorphism is SNPs rs3758650 or rs10902179.

* * * * *

SEQUENCE LISTING

<160> NUMBER OF SEQ ID NOS: 5

<210> SEQ ID NO 1
<211> LENGTH: 21
<212> TYPE: RNA
<213> ORGANISM: Artifical sequence
<220> FEATURE:
<223> OTHER INFORMATION: sense siRNA

<400> SEQUENCE: 1
guguuuacga ggaacccuat t                    21

<210> SEQ ID NO 2
<211> LENGTH: 21
<212> TYPE: RNA
<213> ORGANISM: Artificial sequence
<220> FEATURE:

```
<223> OTHER INFORMATION: Antisense siRNA

<400> SEQUENCE: 2
uaggguuccu cguaaacacg g                                              21

<210> SEQ ID NO 3
<211> LENGTH: 187
<212> TYPE: DNA
<213> ORGANISM: Mus Musculus
<220> FEATURE:
<223> OTHER INFORMATION: Promoter sequence

<400> SEQUENCE: 3
gttcagagaa aggctgggct gcttgttgct ggctaaagga caaagggtaa gtttcaggaa    60
gcagaagagt gagcagatga aattcagcac tgggatcagg ggagtgtctg atttgcaaaa   120
ggaaagtgca aagacagctc ctccttctg aggaaacgaa accaacagca gtccaagctc    180
agtcagc                                                             187

<210> SEQ ID NO 4
<211> LENGTH: 181
<212> TYPE: DNA
<213> ORGANISM: Mus Musculus
<220> FEATURE:
<223> OTHER INFORMATION: Promoter sequence

<400> SEQUENCE: 4
agatgagaga gcagtgaggg agagacagag actcgaattt ccggaggcta tttcagtttt    60
cttttccgtt ttgtgcaatt tcacttatga taccggccaa tgcttggttg ctattttgga   120
aactcccctt aggggatgcc cctcaactgg ccctataaag ggccagcctg agctgcagag   180
g                                                                   181

<210> SEQ ID NO 5
<211> LENGTH: 143
<212> TYPE: DNA
<213> ORGANISM: Mus Musculus
<220> FEATURE:
<223> OTHER INFORMATION: Promoter sequence

<400> SEQUENCE: 5
gataggagct taaataaaga gttttagaaa ctactaaaat gtaaatgaca taggaaaact    60
gaaagggaga agtgaaagtg ggaaattcct ctgaatagag agaggaccat ctcatataaa   120
taggccatac ccatggagaa agg                                           143
```